United States Patent
Honda et al.

(10) Patent No.: US 9,778,206 B2
(45) Date of Patent: Oct. 3, 2017

(54) DEFECT INSPECTION DEVICE AND DEFECT INSPECTION METHOD

(71) Applicant: HITACHI HIGH-TECHNOLOGIES CORPORATION, Minato-ku, Tokyo (JP)

(72) Inventors: Toshifumi Honda, Tokyo (JP);
Takahiro Urano, Tokyo (JP);
Hidetoshi Nishiyama, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/764,985

(22) PCT Filed: Jan. 16, 2014

(86) PCT No.: PCT/JP2014/050708
§ 371 (c)(1),
(2) Date: Jul. 31, 2015

(87) PCT Pub. No.: WO2014/119376
PCT Pub. Date: Aug. 7, 2014

(65) Prior Publication Data
US 2015/0369752 A1   Dec. 24, 2015

(30) Foreign Application Priority Data

Jan. 31, 2013 (JP) ................................ 2013-016909

(51) Int. Cl.
*G01N 21/00* (2006.01)
*G01N 21/88* (2006.01)
(Continued)

(52) U.S. Cl.
CPC ..... *G01N 21/8851* (2013.01); *G01N 21/9501* (2013.01); *G01N 21/956* (2013.01);
(Continued)

(58) Field of Classification Search
CPC ....... G01N 2021/8887; G01N 21/8851; G01N 21/9501; G01N 21/956
(Continued)

(56) References Cited

U.S. PATENT DOCUMENTS 7,037,735 B2   5/2006   Noguchi et al.
7,221,992 B2   5/2007   Smith et al.
(Continued)

FOREIGN PATENT DOCUMENTS

JP   3566589 B2      9/2004
JP   2006-98155 A    4/2006
(Continued)

*Primary Examiner* — Sunghee Y Gray
(74) *Attorney, Agent, or Firm* — Miles & Stockbridge P.C.

(57) ABSTRACT

In an defect inspection method and device, in order to detect a minute defect present on a surface of a sample with a high degree of sensitivity, a defect inspection method includes imaging the same region of a sample in a plurality of image acquisition conditions and acquiring a plurality of images, processing the plurality of acquired images and extracting a defect candidate, clipping a partial image including the extracted defect candidate and a neighboring image of the defect candidate from the acquired images based on position information of the extracted defect candidate, obtaining feature quantities of the defect candidates in the plurality of clipped partial images, associating the defect candidates that have the same coordinates on the sample and are detected in different image acquisition condition, extracting a defect from among the associated defect candidates in a multi-dimensional feature quantity space, and outputting information of the extracted defect.

8 Claims, 29 Drawing Sheets

(51) Int. Cl.
  *G01N 21/956* (2006.01)
  *G01N 21/95* (2006.01)
(52) U.S. Cl.
  CPC ............... *G01N 2021/8887* (2013.01); *G01N 2021/9513* (2013.01)
(58) Field of Classification Search
  USPC ..................................................... 356/237.2
  See application file for complete search history.

(56) References Cited

U.S. PATENT DOCUMENTS

| | | |
|---|---|---|
| 7,283,659 B1 | 10/2007 | Bakker et al. |
| 2006/0078189 A1 | 4/2006 | Hosoya et al. |
| 2008/0285023 A1 | 11/2008 | Tsai et al. |
| 2012/0002860 A1 | 1/2012 | Sakai et al. |
| 2012/0141012 A1 | 6/2012 | Sakai et al. |
| 2013/0294677 A1 | 11/2013 | Urano et al. |

FOREIGN PATENT DOCUMENTS

| | | |
|---|---|---|
| JP | 2010-151824 A | 7/2010 |
| JP | 2011-47724 A | 3/2011 |
| JP | 2012-112915 A | 6/2012 |

F I G. 2
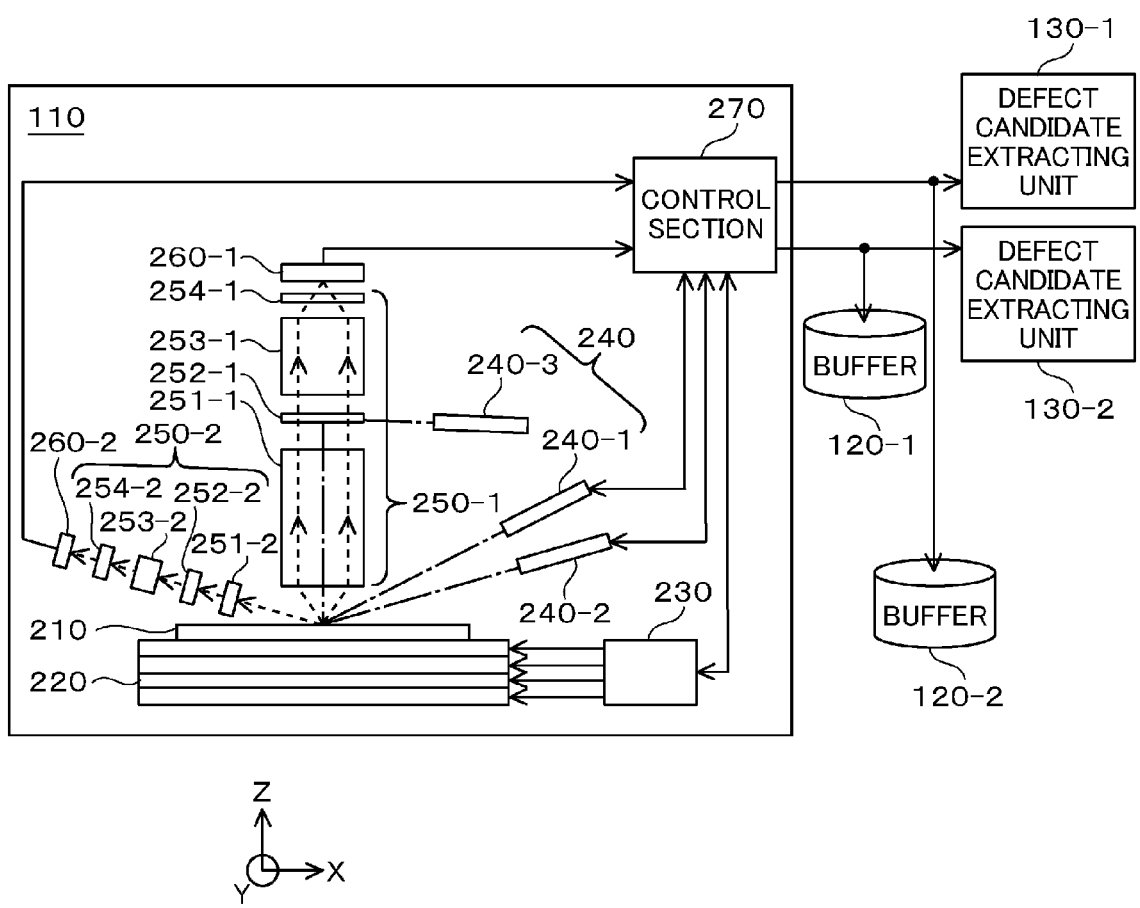

F I G. 3 B
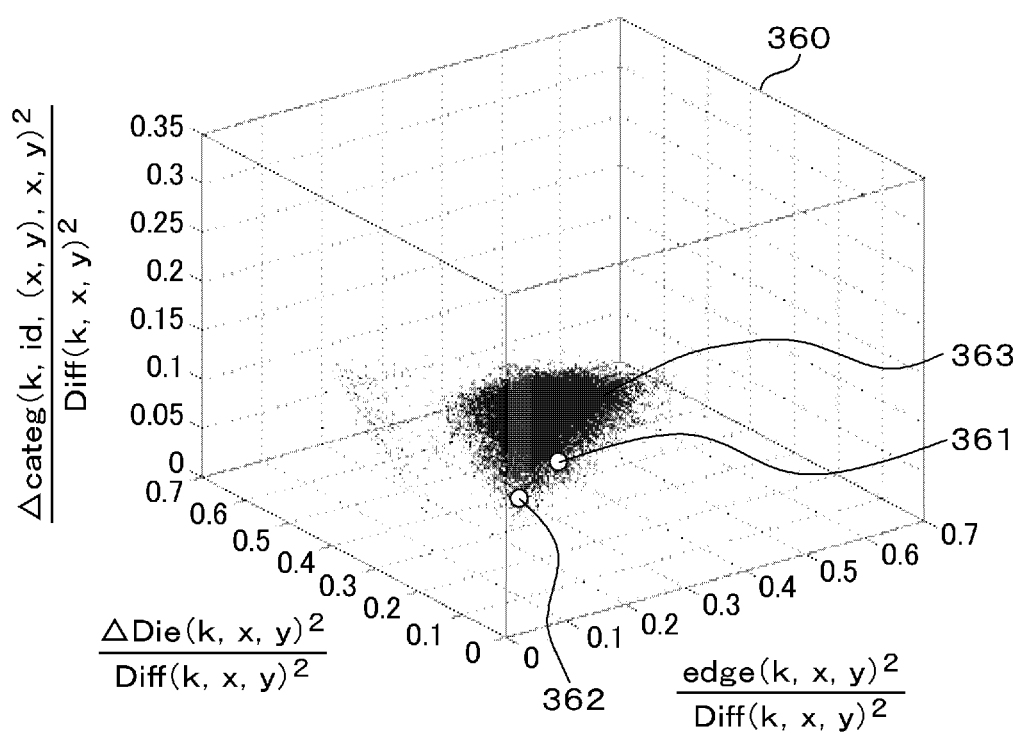

F I G. 1 0 C
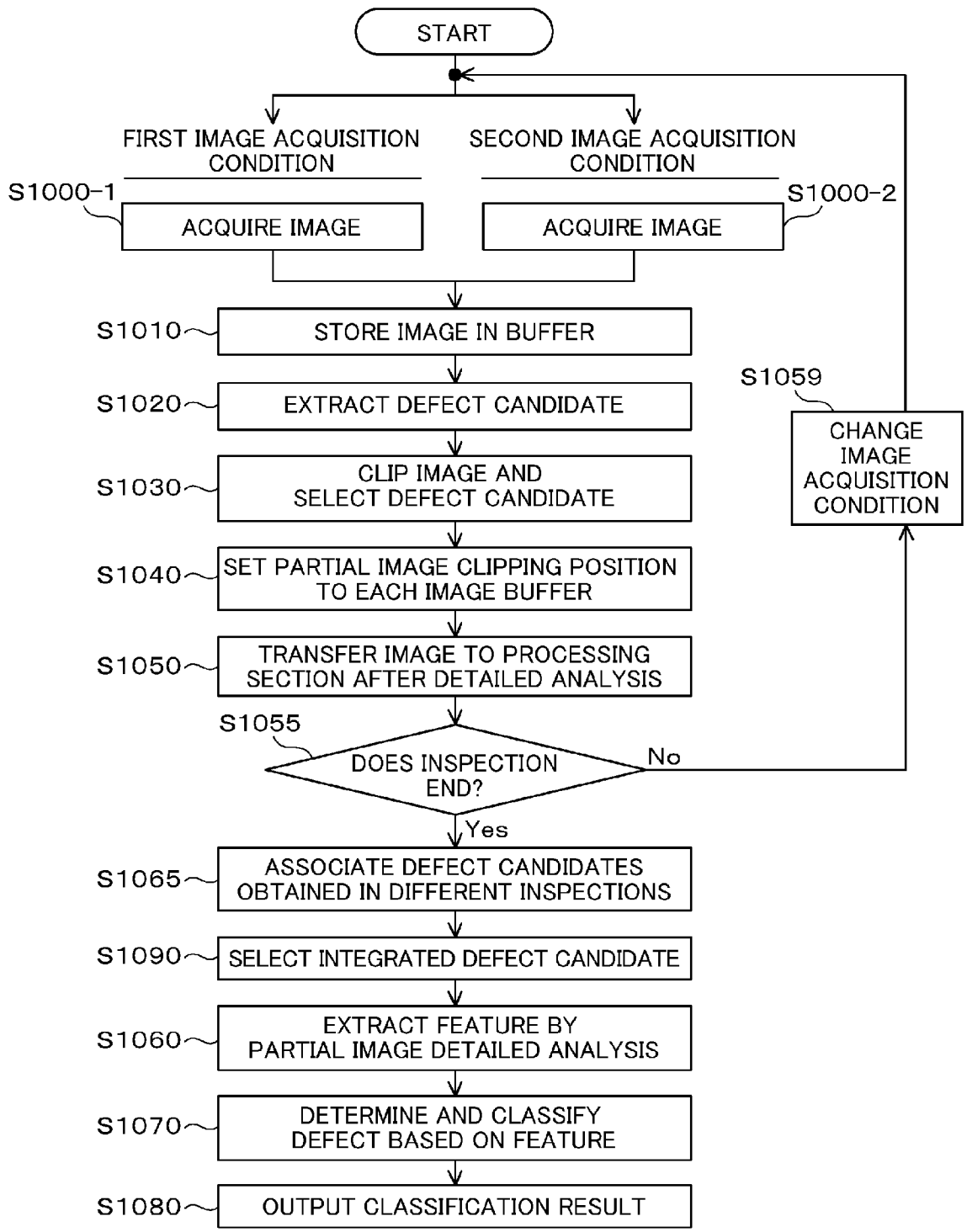

F I G. 1 0 D
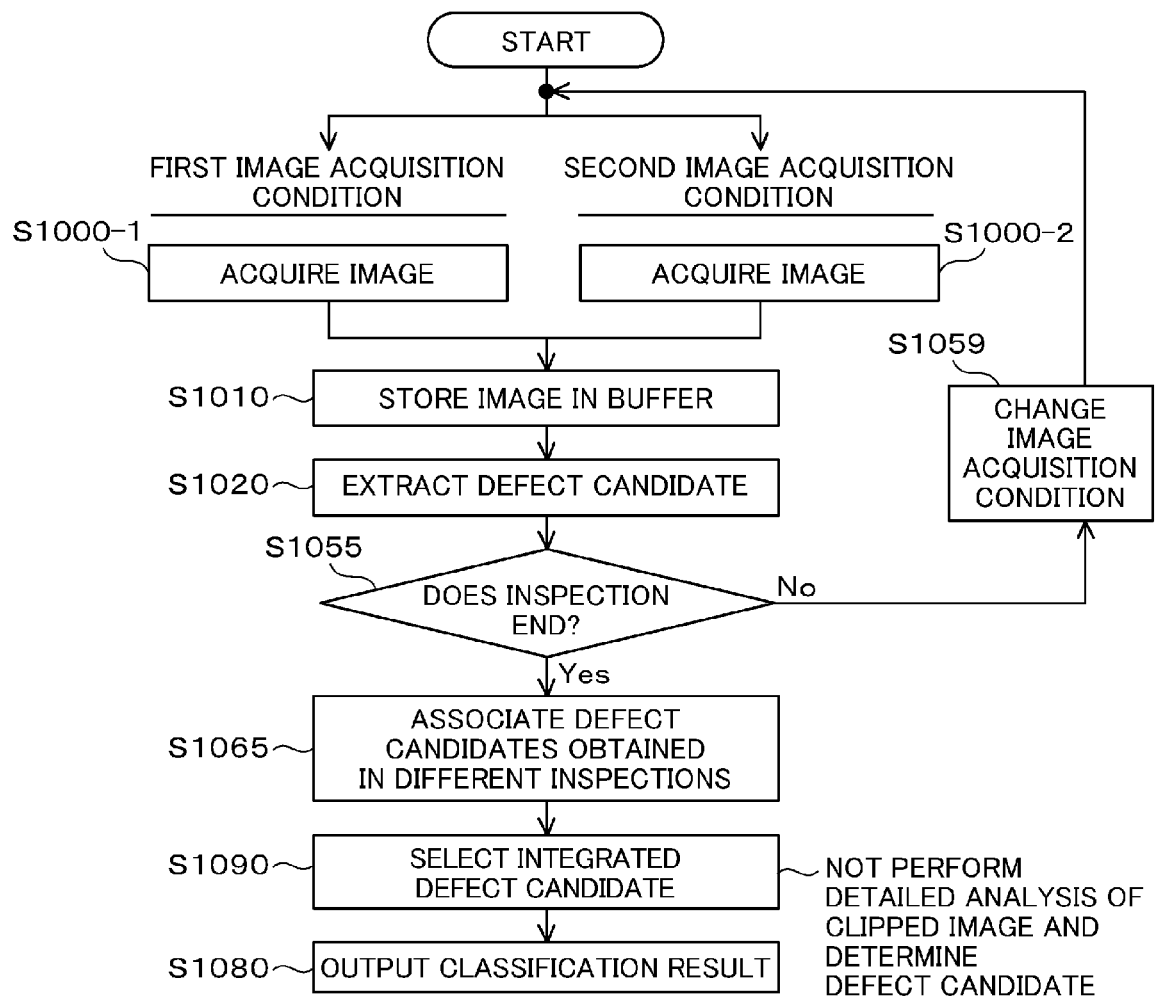

F I G. 1 0 E
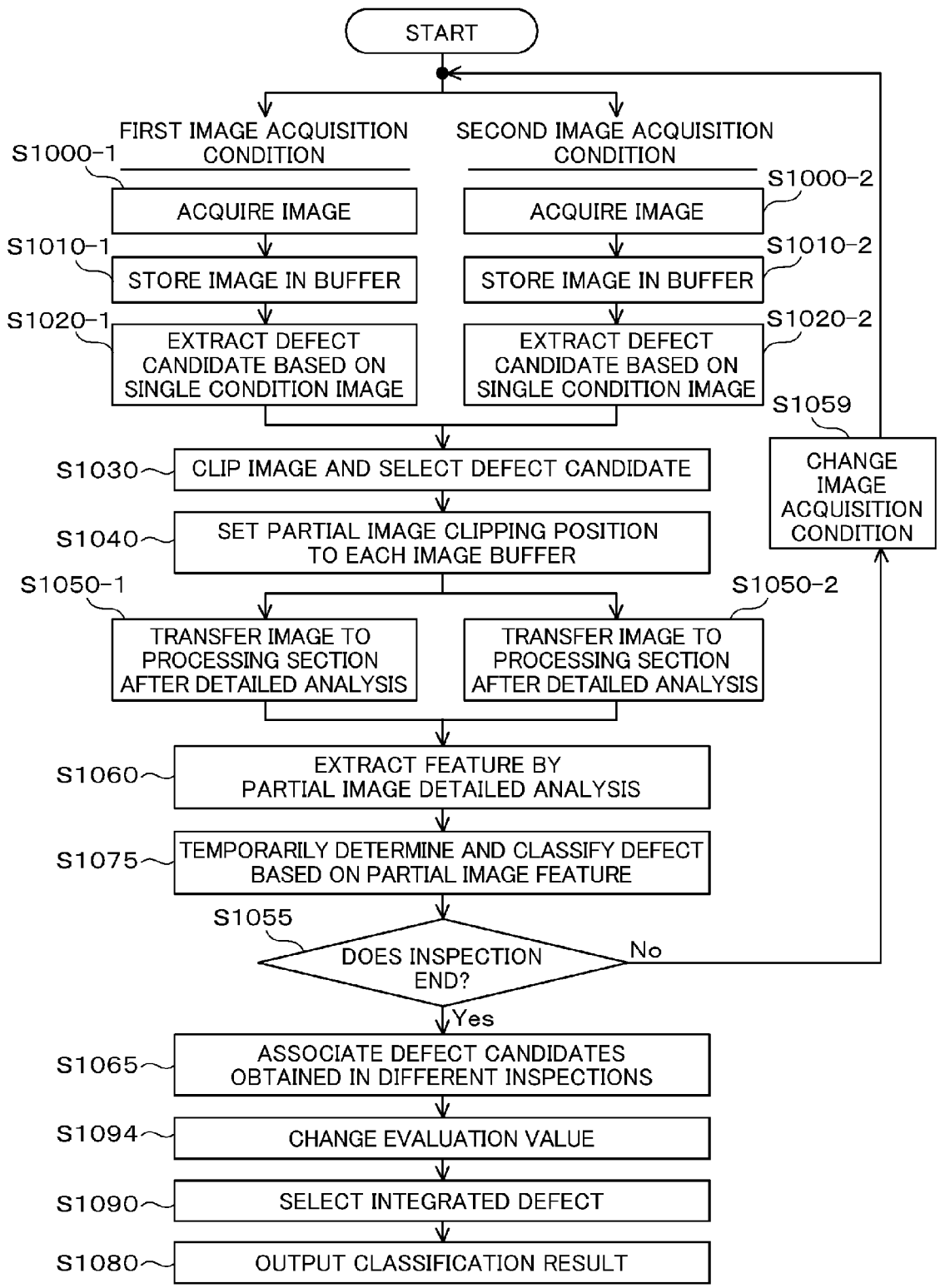

F I G. 1 3 B
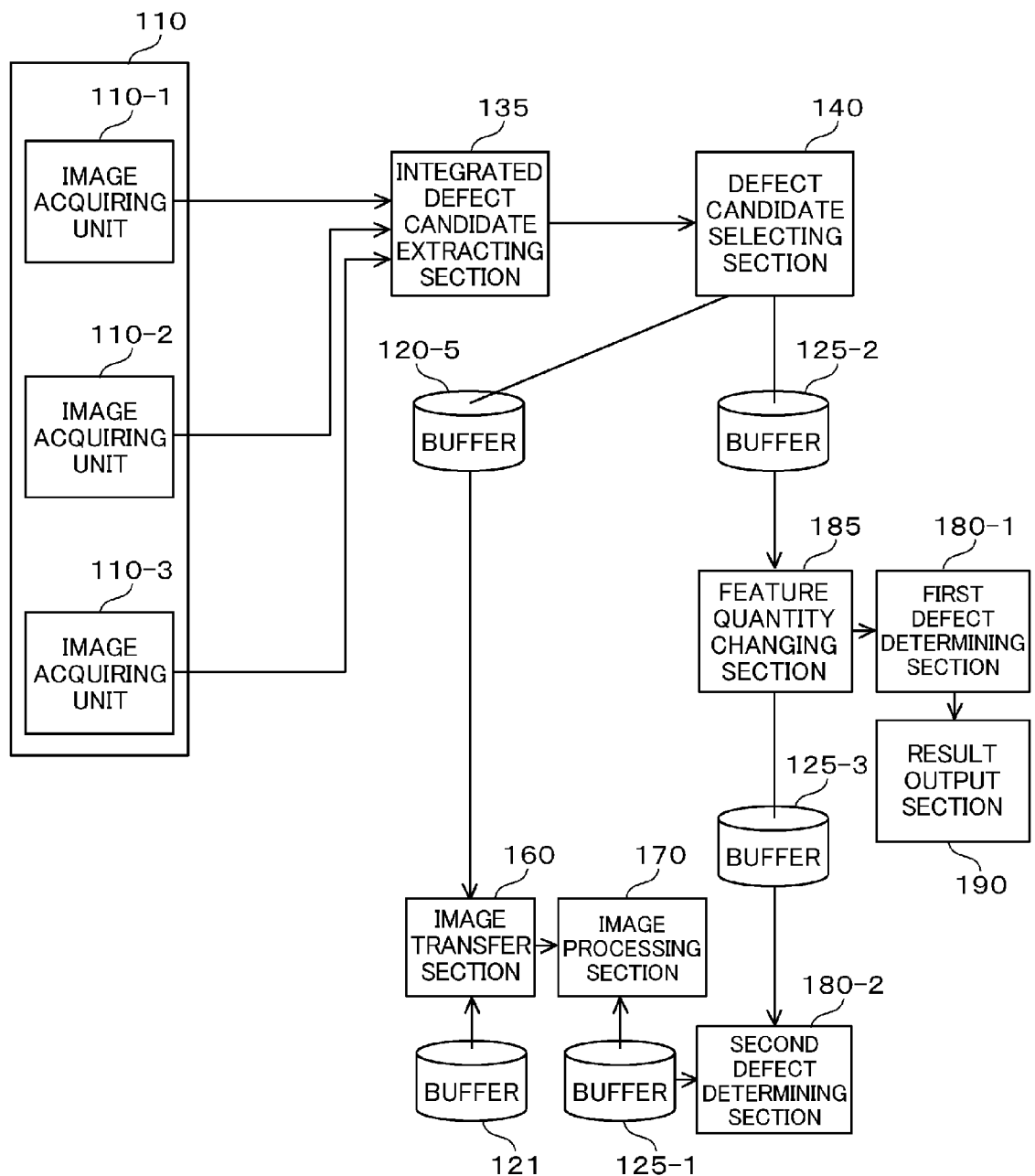

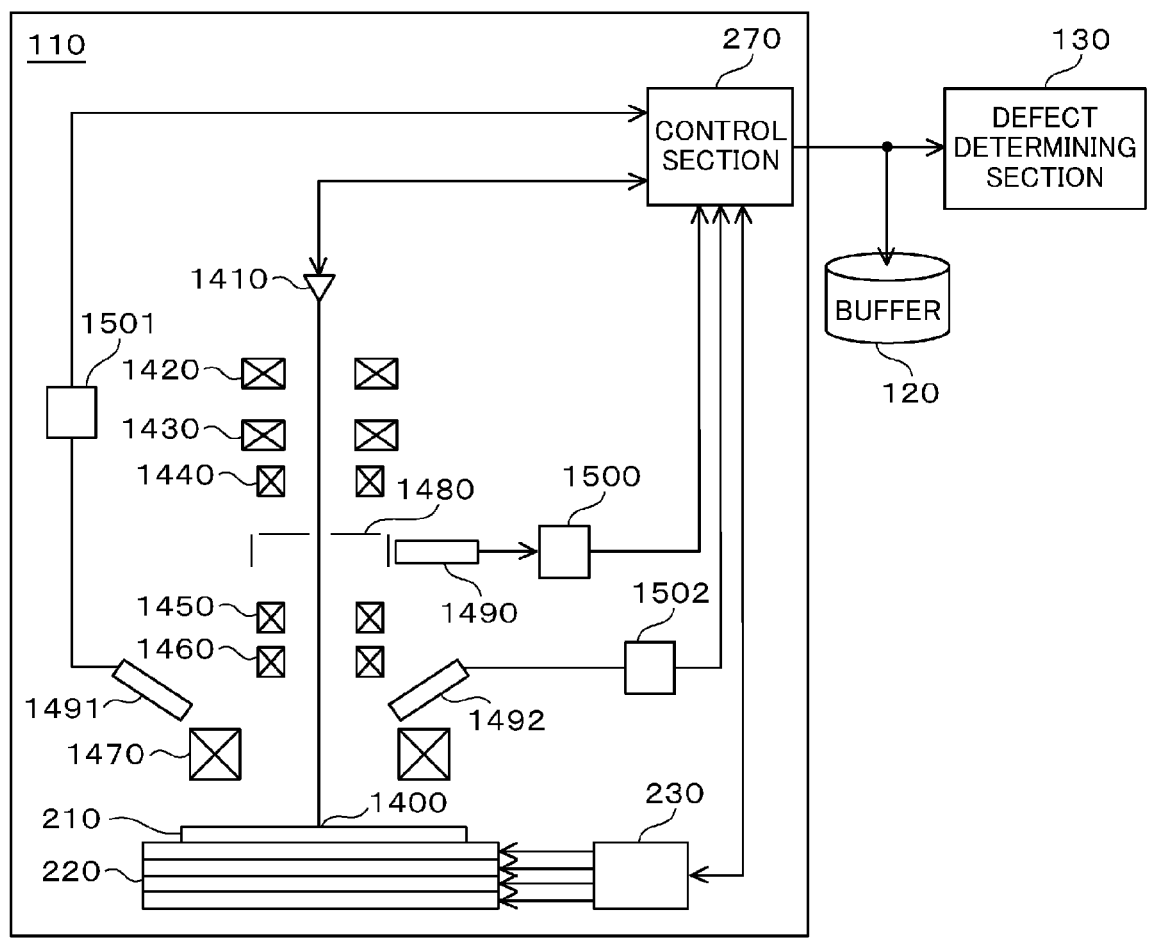
F I G. 1 4

FIG. 15

| | | 1501 | 1502 | 1503 | 1504 | 1505 | 1506 |
|---|---|---|---|---|---|---|---|

| DEFECT # | INSPECTION # | COORDINATES | 126-2 | 181-2 | 185 |
|---|---|---|---|---|---|
| 1 | 1 | — | — | — | — |
| | 2 | X11, Y11 | s1 | SCRATCH (H1) | H1S1 |
| | | X12, Y12 | s2 | | H1S2 |
| | | X13, Y13 | s3 | | H1S3 |
| | | X14, Y14 | s4 | | H1S4 |
| | 3 | — | — | — | — |
| | 4 | X12, Y12 | s5 | NEGATIVE (H2) | H2S5 |
| 2 | 1 | — | — | — | — |
| | 2 | X2, Y2 | s6 | NEGATIVE (H3) | H3S6 |
| | 3 | X2, Y2 | s7 | NEGATIVE (H4) | H4S7 |
| | 4 | — | — | — | — |
| 3 | 1 | X3, Y3 | s8 | — | H0S8 |
| | 2 | X3, Y3 | s9 | — | H0S9 |
| | 3 | X3, Y3 | s10 | NEGATIVE (H5) | S10 |
| | 4 | — | — | — | — |

F I G. 1 6
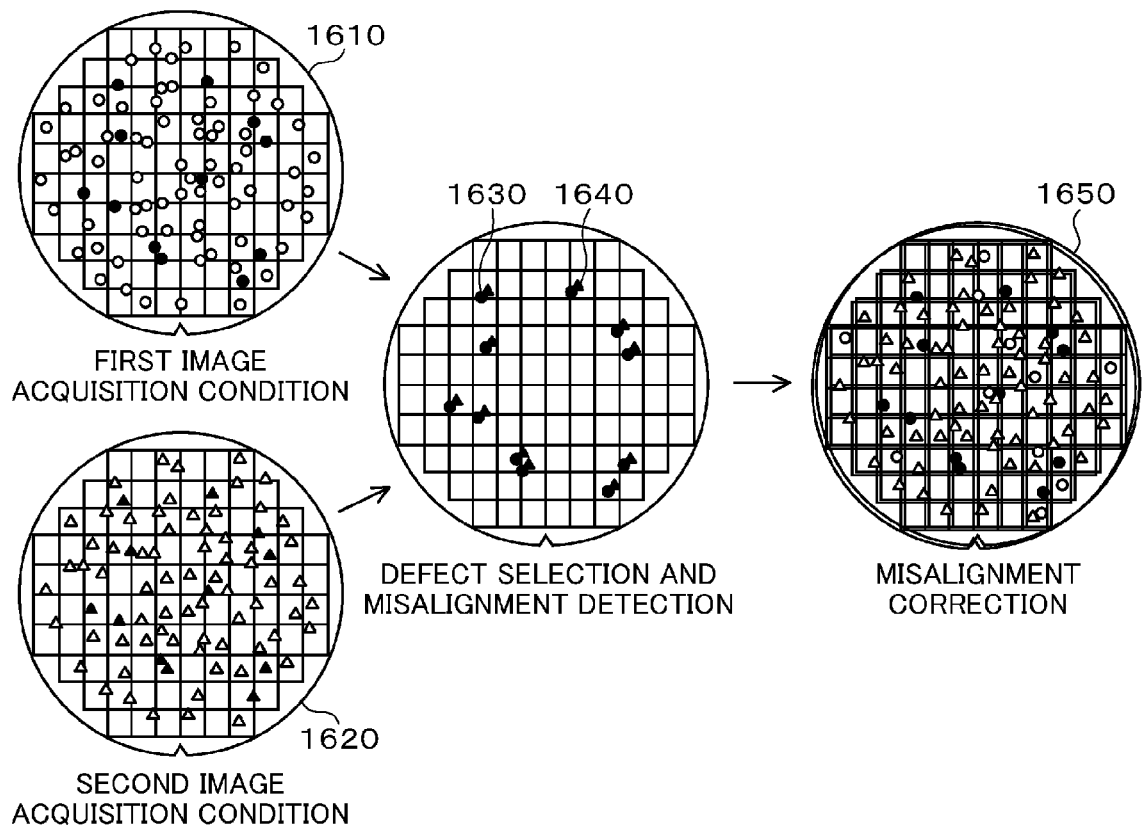

DEFECT INSPECTION DEVICE AND DEFECT INSPECTION METHOD

BACKGROUND

The present invention relates to a defect inspection device and a defect inspection method, which are capable of inspecting a minute defect present on a sample surface with a high degree of sensitivity.

Thin film devices such as semiconductor wafers, liquid crystal displays (LCDs), or hard disk magnetic heads are manufactured through a number of processing processes. In manufacturing of such thin film devices, for the purpose of yield improvement and stability, an external appearance inspection is performed for each series of processes.

Patent Document 1 (JP 3566589 B1) discloses a method of "detecting a defect such as a pattern defect or an alien substance in corresponding regions of two patterns formed to have the same shape originally based on a reference image and an inspection image obtained using lamp light, laser beams, or electron beams in an external appearance inspection."

Further, Patent Document 2 (JP 2006-98155 A) discloses "an inspection method capable of deriving an optimal inspection condition by extracting a defect of interest (DOI) efficiently and teaching it in a situation in which a small number of DOIs are included in a large number of nuisances."

Further, as a technique of improving inspection sensitivity, Patent Document 3 (U.S. Pat. No. 7,221,992) and Patent Document 4 (US 2008/0285023 A) disclose "a method of detecting images according to a plurality of different optical conditions simultaneously, performing a brightness comparison with a reference image for each condition, integrating comparison values, and distinguishing a defect and a noise," but a problem lies in that a high data transfer rate for transmitting a defect image acquired at a high resolution in each optical condition to a defect determining section is necessary, and a processor of high processing performance for processing images of a plurality of conditions once is necessary.

Patent Document 5 (U.S. Pat. No. 7,283,659) discloses "a method of performing efficient defect classification through two-step determination, that is, classification of defect candidates by a non-image feature such as process information and classification by a defect image feature."

Patent Document 6 (JP 2012-112915 A) discloses a method of extracting a defect candidate from each of images detected in a plurality of imaging conditions, extracting a detailed feature quantity by processing a narrow region image centering on a defect candidate in any one condition or all imaging conditions based on a determination result obtained by integrating feature quantities obtained by processing respective images, and determining a defect based on the feature quantity.

CITATION LIST

Patent Document

Patent Document 1: JP 3566589 B1
Patent Document 2: JP 2006-98155 A
Patent Document 3: U.S. Pat. No. 7,221,992
Patent Document 4: US 2008/0285023 A
Patent Document 5: U.S. Pat. No. 7,283,659
Patent Document 6: JP 2012-112915 A

SUMMARY

In the technique of the related art, basically, an inspection image is compared with the same reference image thereas, and a region having a large difference is detected as a defect. In the defect detection, there are a detection condition in which detection is easy and a detection condition in which detection is difficult according to a region having a defect or an attribute of a defect, and in the inspection based on one detection condition as in Patent Documents 1 and 2, it is difficult to implement an inspection of performing simultaneous detection regardless of a type of a defect. Thus, a technique of using a plurality of optical conditions is necessary. In the technique disclosed in Patent Document 3, a detection method is not mentioned, but in the technique disclosed in Patent Document 4, both of a bright-field image and a dark-field image are simultaneously acquired.

However, generally, when a defect is detected in a bright-field image, only a defect having a size that is equal to a pixel size of a detecting sensor or a fraction thereof is detected, but in a dark-field image, it is possible to detect up to a detect having a size of a tenth thereof or less. Since an imaging period of time of a sensor is commonly proportional to a pixel size, when an appropriate pixel size is set in a bright-field image, it is difficult to implement a high-speed inspection that is a characteristic of a dark-field image, and when an appropriate pixel size is set in detection of a dark-field image, a pixel size has to be increased even in a bright-field image due to a restriction of an imaging period of time of a sensor, and only a low-sensitivity inspection can be implemented. In other words, when a bright-field inspection and a dark-field inspection are simultaneously performed, there is a gap in a throughput, and it is difficult to perform an appropriate inspection. Further, for example, in a dark-field inspection or an inspection combined with a dark-field, a defect to be detected changes according to an azimuth angle of an illumination, polarized light, or the like, and thus, in a dark-field inspection, it is difficult to improve a defect capture ratio sufficiently although a plurality of detection systems are equipped in one illumination condition.

For this reason, a method of performing inspections of multiple times sequentially and combining inspection results is considered, but in this case, it is difficult to simply apply a technique of integrating and inspecting difference results of a plurality of detection systems as illustrated in FIG. 7 in Patent Document 4). When inspection results of multiple times are integrated, it is difficult to obtain a correspondence relation of inspections of multiple times of each pixel unless a very large amount of data is acquired in a single inspection and stored. In order to implement it completely, for example, an external storage such as a large capacity hard disk is necessary, and thus a system is complicated, and a throughput decreases.

In the technique disclosed in Patent Document 5, since defect determination is performed for each image acquired in each detection system, for integration of data of a plurality of detection systems of each pixel, it is difficult to use a technique of integrating evaluation results of a plurality of detection systems illustrated in FIG. 7 of Patent Document 4 in inspections of all detection conditions. Due to the same reason, when the method disclosed in Patent Document 2 is extended to an inspection of multiple detections, although an attempt to determine both a detection system defect and a nuisance based on an image feature quantity calculated after sequential defect determination is made, since there is no case in which both a defect and a nuisance are imaged in both detection systems, a defect candidate in which it is difficult to plot a feature quantity has occurred.

In Patent Document 6, when an evaluation value is exceeded, a narrow region image is processed from among accumulated images based on defect feature quantities obtained in images photographed in a plurality of detection conditions, but when the same target is inspected multiple times, if nothing is found after scanning is performed multiple times, it is difficult to perform the determination, and thus a huge image photographing buffer is necessary, and it was actually possible to apply only when an image is photographed in a plurality of conditions in parallel.

The present invention was made to solve the problems of the technique of the related art, and it is desirable to provide a defect inspection method and device, which are capable of detecting a minute defect present on a surface of a sample with a high degree of sensitivity using a plurality of inspection conditions.

In order to solve the above problems, the present invention provides a defect inspection method which includes imaging the same region of a sample in a plurality of image acquisition conditions and acquiring a plurality of images for the same region of the sample, processing the plurality of acquired images of the sample and extracting a defect candidate in each of the plurality of images, clipping a partial image including the extracted defect candidate and a neighboring image of the defect candidate from the plurality of acquired images based on position information of the extracted defect candidate, obtaining feature quantities of the defect candidates in the plurality of clipped partial images, associating the defect candidates that have the same coordinates and are detected in conditions in which the image acquisition condition is different among the extracted defect candidate, extracting a defect from among the associated defect candidates based on multi-dimensional feature quantity space data of feature quantities of the associated defect candidates, and outputting information of the extracted defect.

Further, in order to solve the above problems, the present invention provides a defect inspection method which includes imaging the same region of a sample in a plurality of image acquisition conditions and acquiring a plurality of images for the same region of the sample, processing the plurality of acquired images and extracting a defect candidate in each of the plurality of images, clipping a partial image including the extracted defect candidate and a neighboring image of the defect candidate from the plurality of acquired images based on position information of the extracted defect candidate, performing the acquiring of the plurality of images, the extracting of the defect candidate, and the clipping of the partial image multiple times while changing the plurality of image acquisition conditions, and associating the defect candidates having the same coordinates on the sample among the defect candidates included in the partial image clipped in the clipping of the partial image from the images obtained by imaging multiple times while changing the plurality of image acquisition conditions, obtaining feature quantities of the associated defect candidates, extracting a defect from among the associated defect candidates based on multi-dimensional feature quantity space data of the feature quantities of the associated defect candidates, and outputting information of the extracted defect.

Furthermore, in order to solve the above problems, the present invention provides a defect inspection device which includes an image acquiring unit that images the same region of a sample in a plurality of image acquisition conditions and acquires a plurality of images for the same region of the sample, a defect candidate extracting unit that processes the plurality of acquired images of the sample acquired by the image acquiring unit and extracts a defect candidate in each of the plurality of images, a partial image clipping unit that clips a partial image including the extracted defect candidate and a neighboring image of the defect candidate from the plurality of images acquired by the image acquiring unit based on position information of the defect candidate extracted by the defect candidate extracting unit, a feature quantity calculating unit that obtains feature quantities of the defect candidates in the plurality of partial images clipped by the partial image clipping unit, a defect candidate associating unit that associates the defect candidates that have the same coordinates and are detected in conditions in which the image acquisition condition is different among the defect candidate extracted by the defect candidate extracting unit, a defect extracting unit that extracts a defect from among the defect candidates associated by the defect candidate associating unit based on multi-dimensional feature quantity space data of feature quantities of the associated defect candidates obtained by the feature quantity calculating unit, and an output unit that outputs information of the defect extracted by the defect extracting unit.

Moreover, in order to solve the above problems, the present invention provides a defect inspection device which includes an image acquiring unit that images the same region of a sample in a plurality of image acquisition conditions and acquires a plurality of images for the same region of the sample, a defect candidate extracting unit that processes the plurality of acquired images acquired by the image acquiring unit and extracts a defect candidate in each of the plurality of images, a partial image clipping unit that clips a partial image including the extracted defect candidate and a neighboring image of the defect candidate from the plurality of images acquired by the image acquiring unit based on position information of the defect candidate extracted by the defect candidate extracting unit, a control unit that controls the image acquiring unit, the defect candidate extracting unit, and the partial image clipping unit such that the acquiring of the plurality of images through the image acquiring unit, the extracting of the defect candidate through the defect candidate extracting unit, and the clipping of the partial image through the partial image clipping unit are performed multiple times while changing the plurality of image acquisition conditions, a defect candidate associating unit that associates the defect candidates having the same coordinates on the sample among the defect candidates included in the partial image clipped by the partial image clipping unit from the images obtained by imaging multiple times while changing the plurality of image acquisition conditions of the image acquiring unit according to the control of the control unit, a feature quantity calculating unit that obtains feature quantities of the defect candidates associated by the defect candidate associating unit, a defect extracting unit that extracts a defect from among the defect candidates associated by the defect candidate associating unit based on multi-dimensional feature quantity space data of the feature quantities of the defect candidates obtained by the feature quantity calculating unit, and an output unit that outputs information of the defect extracted by the defect extracting unit.

According to the invention disclosed in this application, it is possible to provide a defect inspection method and a defect inspection device, which are capable of inspecting a minute defect present on a sample surface with a high degree of sensitivity.

BRIEF DESCRIPTION OF THE DRAWINGS

FIG. 2 is a block diagram illustrating an exemplary configuration of an image acquiring section in the defect inspection devices according to the first embodiment and the first and second modified examples of the present invention.

FIG. 3B is a three-dimensional scatter diagram for describing a defect candidate extracting method in the defect inspection devices according to the first embodiment and the first and second modified examples of the present invention.

FIG. 10C is a diagram illustrating an example of a defect determination flow in the defect inspection devices according to the first embodiment and the first and second modified examples of the present invention, and illustrates a flowchart when a plurality of images are acquired while changing an image acquisition condition, and the acquired images are temporarily stored in a common buffer.

FIG. 10D is a diagram illustrating an example of a defect determination in the defect inspection devices according to the first embodiment and the first and second modified examples of the present invention, and illustrates a flowchart when a plurality of images are acquired while changing an image acquisition condition, and a defect candidate is determined without performing detailed analysis of a clipped image.

FIG. 10E is a diagram illustrating an example of a defect determination flow in the second modified example of the first embodiment of the present invention, and illustrates a flowchart of a process in which a plurality of images are acquired while changing an image acquisition condition, defect candidates obtained in different inspections are associated, and then defect determination is performed.

FIG. 13B is a block diagram illustrating an exemplary configuration of a form of a defect inspection device according to a modified example of the third embodiment of the present invention.

FIG. 14 is a block diagram illustrating a schematic configuration of an SEM type inspection device according to a fourth embodiment of the present invention.

FIG. 15 is a diagram of a data sheet illustrating an inspection data output example of the defect inspection devices according to the first embodiment and the first and second modified examples of the present invention.

FIG. 16 is a diagram of a defect candidate map illustrating an example of misalignment detection and correction in a first defect determining section in the defect inspection devices according to the first to third embodiments of the present invention.

DESCRIPTION OF THE PREFERRED EMBODIMENTS

Figure 1A:
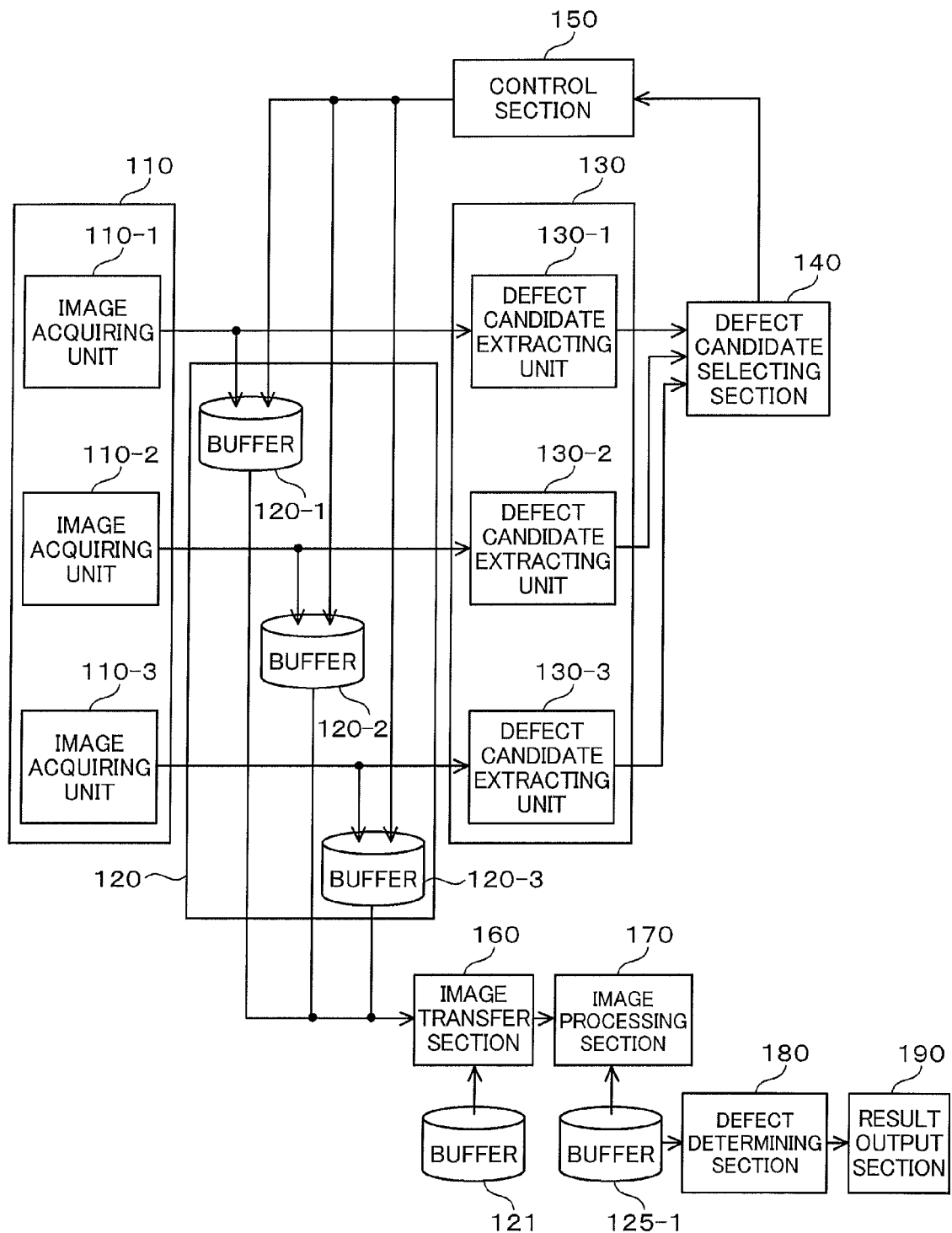
FIG. 1A is a block diagram illustrating an overall schematic configuration of a defect inspection device according to a first embodiment of the present invention.

The present invention makes it possible to inspect a minute defect at a high speed with a high degree of sensitivity without increasing image data by extracting a defect candidate from each of images acquired in a plurality of image acquisition conditions and processing the extracted defect candidates among a plurality of images in an integrated manner.

Hereinafter, embodiments of the present invention will be described in detail with reference to the appended drawings. In all drawings for describing embodiments, the same members are denoted by the same reference numerals in principle, and a repeated description will be omitted.

First Embodiment

Hereinafter, a defect inspection technique (a defect inspection method and a defect inspection device) according to a first embodiment of the present invention will be described in detail with reference to FIGS. 1 to 11.

As a pattern inspection technique according to the first embodiment of the present invention, a defect inspection device and a defect inspection method based on a dark-field illumination targeted at a semiconductor wafer will be described as an example.

FIG. 1A illustrates an exemplary configuration of the defect inspection device according to the first embodiment. The defect inspection device according to the first embodiment includes an image acquiring section 110 (image acquiring units 110-1, 110-2, and 110-3), an image storing buffer section 120 (image storing buffers 120-1, 120-2, 120-3, and 120-4), a feature quantity storing buffer 125 (125-1), a defect candidate extracting section 130 (defect candidate extracting units 130-1, 130-2, and 130-3), a defect candidate selecting section 140, a control section 150, an image transfer section 160, an image processing section 170, a defect determining section 180, and a result output section 190.

In the image acquiring section 110, the image acquiring units 110-1, 110-2, and 110-3 acquire inspection image data of a semiconductor wafer serving as an inspection object, and transfer the image data to the image storing buffers 120-1, 120-2, and 120-3 of the image storing buffer section 120 and the defect candidate extracting units 130-1, 130-2, and 130-3 of the defect candidate extracting section 130. The defect candidate extracting units 130-1, 130-2, and 130-3 of the defect candidate extracting section 130 extract defect candidates from the image data transferred from the image acquiring units 110-1, 110-2, and 110-3 of the image acquiring section 110 through a process which will be described later, and transfers the defect candidates to the defect candidate selecting section 140. The defect candidate selecting section 140 removes misinformation serving as erroneous detection such as a noise or a nuisance which the user does not desire to detect from the defect candidates, and transmits remaining defect candidate information to the control section 150.

The control section 150 that has received the defect candidate information from the defect candidate selecting section 140 transmits coordinate information of the remaining defect candidate to the image storing buffers 120-1, 120-2, and 120-3 of the image storing buffer section 120. In the image storing buffer section 120, an image including the defect candidate is clipped from the image data that are input from the image acquiring section 110 and stored in the image storing buffers 120-1, 120-2, and 120-3 based on the coordinate information of the defect candidate received from the control section 150, and the clipped image including the defect candidate is transferred to the image transfer section 160. The image transfer section 160 stores the image including the defect candidate transferred from the image storing buffers 120-1, 120-2, and 120-3 in a buffer 121.

In the pattern inspection according to the present embodiment, a sample serving as an inspection target is inspected multiple times. In other words, a clipped image including a defect candidate acquired by inspections of multiple times (a plurality of inspection conditions) is stored in the buffer 121 illustrated in FIG. 1A. The image data has a size of 32×32 which meets a typical defect size, for example, and is data of a reference image that is an image of the same design section as an inspection image. The image accumulated in the buffer 121 is transferred to the image processing section 170. The image processing section 170 calculates a feature quantity vector comprised of one or more features among an image feature quantity of the defect candidate, that is, differential brightness between the inspection image and the reference image, a brightness of a defect portion of a differential image between the inspection image and the reference image, the texture of the differential image, a shape feature quantity of the defect portion, and a pattern shape of the defect portion of the differential image, and stores the feature quantity vector in a buffer 125-1. The feature quantity vector is transferred to the defect determining section 180, and defect determination is performed in a multi-dimensional feature space.

In order to distinguish a defect from a nuisance in the multi-dimensional feature space, a well-known classification technique, for example, any one of a binary tree, a support vector machine, a Mahalanobis distance technique, and a neural network or a combination thereof is used. Through this determination, only a DOI serving as a defect which the user desires to detect is extracted, and the DOI is output to the result output section 190.

FIG. 1A illustrates a configuration in which the image storing buffers 120-1, 120-2, and 120-3 and the defect candidate extracting sections 130-1, 130-2, and 130-3 are provided to correspond to the image acquiring sections 110-1, 110-2, and 110-3 that perform image acquisition in three different inspection image acquisition conditions in a one-to-one manner. Here, the inspection image acquisition condition includes an illumination condition (an incident direction of illumination light on a sample, a wavelength of illumination light, a polarization state of illumination light, or the like) on a sample, a detection condition (a detection direction of reflected scattering light from a sample, a detection wavelength region, a polarization state, or the like), and inspection image acquisitions at different detection sensitivities.

Figure 1B:
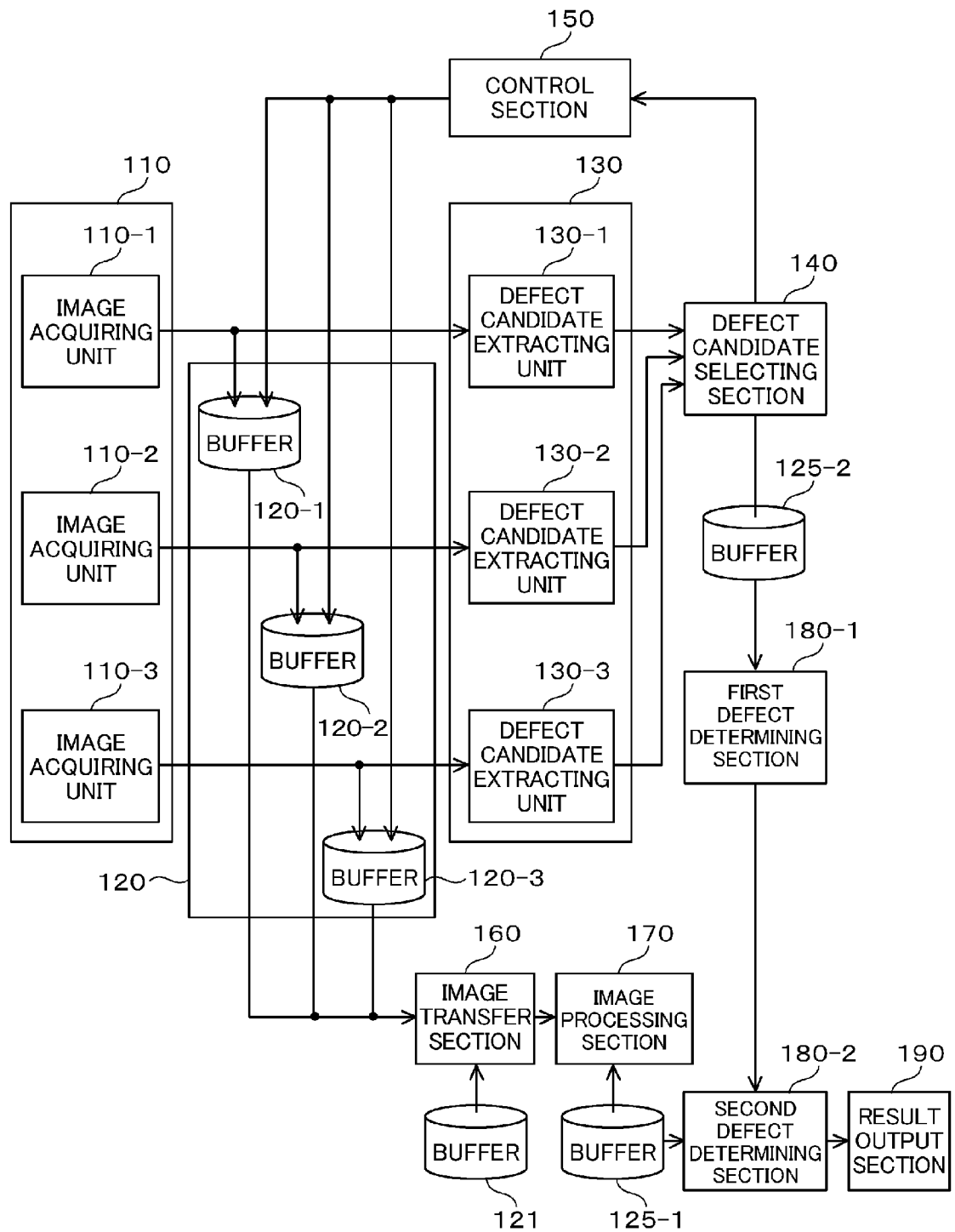
FIG. 1B is a block diagram illustrating an overall schematic configuration of a defect inspection device according to a first modified example of the first embodiment of the present invention.

FIG. 1B illustrates an extension of the defect inspection configuration according to the first embodiment described with reference to FIG. 1A (a first modified example). In a minute DOI, particularly, in a fine short circuit called a short circuit of a groove bottom or a hair short circuit, it is difficult to reveal a defect, and it is difficult to reveal it in a condition other than a specific detection condition. In the present invention, a capture ratio of a DOI is improved by performing inspection multiple times in a plurality of different imaging conditions, but for a defect in which it is difficult to reveal, it is difficult to detect a defect in all inspections.

In the defect inspection configuration according to the first embodiment described with reference to FIG. 1A, the three image acquiring sections that can perform detection in parallel are equipped, but if it is possible to reveal a defect only in inspections of N times among inspections of M times, only 3N clipped images are obtained as the clipped image of the defect candidate stored in the buffer 121. Since the number of clipped images to be obtained in each defect candidate is unknown, it is difficult to expect high performance by application of the Mahalanobis distance technique or the support vector machine that performs distinguishing in view of a dimension number of a specific feature vector.

In this regard, in the configuration of the defect inspection device according to the first modified example illustrated in FIG. 1B, a multi-dimensional feature classifier that does not use the clipped image of the buffer 121 is equipped. 125-2 indicates a feature quantity storing buffer, and the feature quantity storing buffer 125-2 stores a feature quantity used for extraction of defect candidates by the defect candidate extracting units 130-1, 130-2, and 130-3 of the defect candidate extracting section. The feature quantity is configured with any one of a difference between the inspection image and the reference image, a brightness variation between dies of the same coordinates, a differential image variation in a pattern similar to the defect candidate of the reference image, and an edge strength of the reference image or a combination thereof. The feature quantity data is stored as much as inspections of M times. Here, the feature quantity storing buffer 125-2 is configured to be able to store more data than the clipped image stored in the buffer 121.

For the image data stored in the buffer 121, since the data typically has the size of 32×32 for example, and both the inspection image and the reference image are necessary, data of 2 KB is necessary for each image acquisition data. However, for data stored in the feature quantity storing buffer 125-2, since a feature quantity vector is, for example, four-dimensional, and data of 8 B is necessary if each data is indicated by a fixed point of 2 bytes, when a buffer having the same capacity is prepared, data of about 150 times can be stored. Further, since the process using the image processing section 170 is unnecessary, the computation cost is basically unnecessary. Thus, the defect candidate selecting section 140 selects the defect candidate such that the number of defect candidates accumulated in the feature quantity storing buffer 125-2 is larger than the number of defect candidates accumulated in the buffer 121 by about double digits.

The defect determining section 180 in the defect inspection device illustrated in FIG. 1A is divided into two in the configuration of the defect inspection device according to the first modified example illustrated in FIG. 1B. A first defect determining section 180-1 performs a determination process in which a determination boundary is set to a multi-dimensional space based on the feature quantity vector of the defect candidate accumulated in the feature quantity storing buffer 125-2, and a second defect determining section 180-2 performs a process based on the feature quantity data that is extracted by the image processing section 170 and accumulated in the buffer 125-1. The second defect determining section 180-2 narrows down the image feature quantity used for determination for each attribute of the defect candidate to be assumed based on the determination result of the first defect determining section 180-1, and reduces a problem in that all clipped images are not prepared for each defect candidate. For example, when a possibility of a scratch of a DOI type is regarded to be high in the first defect determining section 180-1, the second defect determining section 180-2 performs the determination using only an image feature quantity for scratch determination, and when a possibility of foreign matter is regarded to be high in the first defect determining section 180-1, the second defect determining section 180-2 performs the determination using only an image feature quantity for foreign matter determination.

Figure 1C:
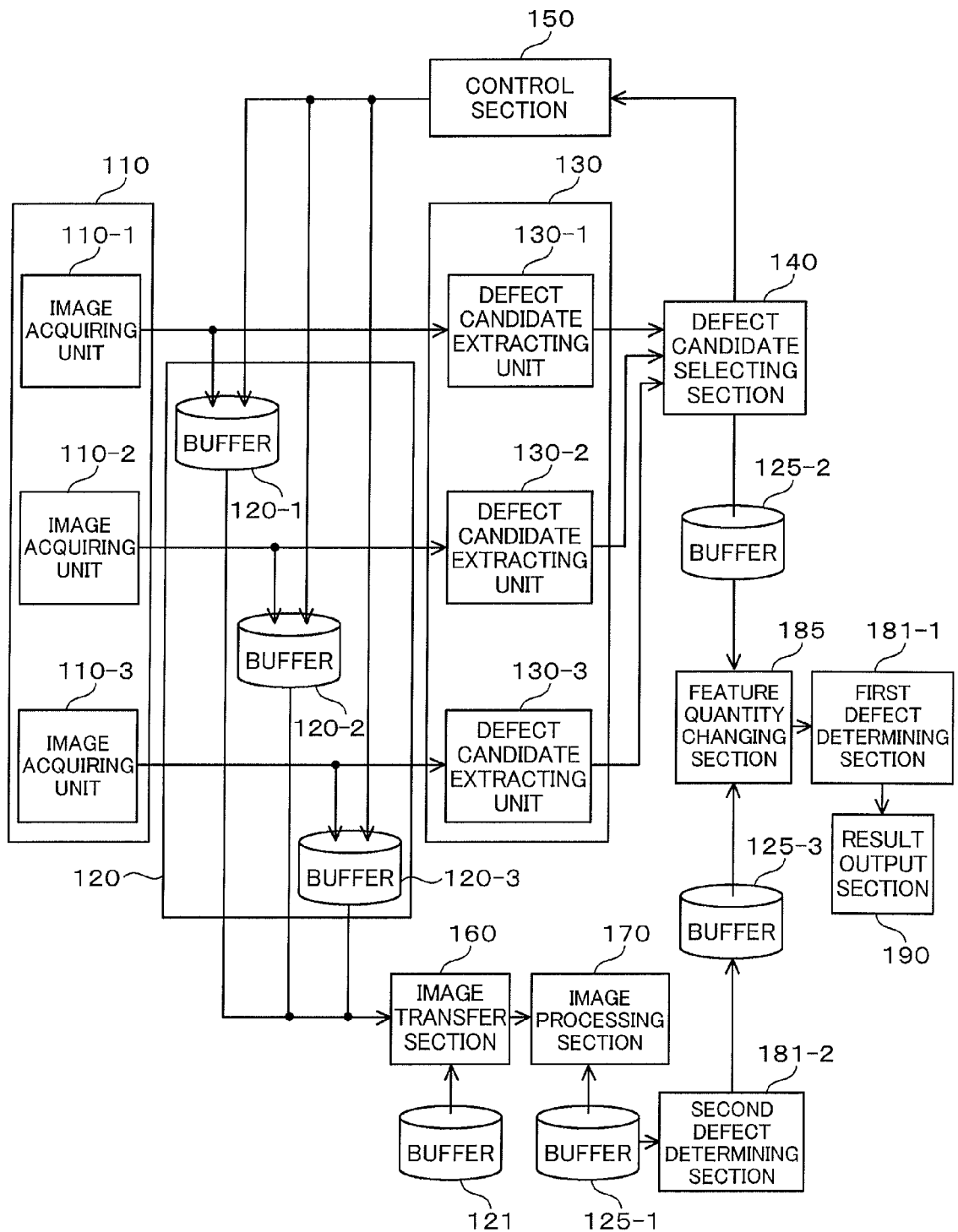
FIG. 1C is a block diagram illustrating an overall configuration of a defect inspection device according to a second modified example of the first embodiment of the present invention.

FIG. 1C illustrates a configuration of a second modified example of the defect inspection device. The defect inspection device of the second modified example illustrated in FIG. 1C has a similar configuration to the configuration of the defect inspection device of the first modified example illustrated in FIG. 1B, but operations of a first defect determining section 181-1 and a second defect determining section 181-2 differ from the operation of the defect inspection device described above with reference to FIG. 1B. In the case of FIG. 1B, the first defect determining section 180-1 performs pre-processing of the second defect determining section 180-2, whereas in the configuration of FIG. 1C, the second defect determining section 181-2 perform pre-processing of the defect determination of the first defect determining section 181-1. The defect determination of the first defect determining section 181-1 is performed in the multi-dimensional feature space based on the feature quantity data accumulated in the buffer 125-1 in certain single inspection among inspections of multiple times, and a temporary determination result is transferred to a buffer 125-3.

In this case, when any one of the defect candidate extracting units 130-1, 130-2, and 130-3 of the defect candidate extracting section 130 extracts a defect candidate at certain coordinates from a specific image, it is possible to perform a setting so that the defect candidate selecting section 140 operates to store a clipped image having corresponding coordinates without exceeding a defect candidate extraction specifying threshold and execute the defect determination of the second defect determining section 181-2 without incurring a problem in that a clipped image of a defect is not prepared. The second defect determining section 181-2 determines an apparent defect, for example, removes a nuisance or determines a scratch defect, and accumulates the determination result in a buffer 126-3.

The buffer 125-3 stores the feature quantity extracted by the image processing section 170 as well. In the image processing section 170, since image processing is performed based on the clipped image, image processing requiring a computation cost higher than image processing for defect candidate extraction in the defect candidate extracting units 130-1, 130-2, and 130-3 of the defect candidate extracting section 130, for example, correction of brightness and contrast of an image, noise reduction, image quality restoration by deconvolution of an image, detailed noise determination by pattern recognition, and the like are performed. Thus, it is possible to calculate a more appropriate result even when the feature quantity is the same as the feature quantity of the defect candidate output through the defect candidate extraction in the defect candidate extracting units 130-1, 130-2, and 130-3 of the defect candidate extracting section 130.

185 indicates a feature quantity converting section, and the feature quantity converting section 185 replaces the feature quantity accumulated by the second defect determining section 181-2 among the feature quantities accumulated in the feature quantity storing buffer 125-2 with the feature quantity accumulated in the buffer 125-3, and multiplies a difference value of the result in which the difference between the inspection image and the reference image serving as an important determination criterion in the defect determination is determined to be large by a gain that is 1 or less and close to 0 or multiplies a brightness variation between dies or a differential image variation by a gain of 1 or more, regardless of whether or not it is determined as a nuisance by the second defect determining section 181-2. As a result, the defect candidate that is accumulated in the buffer 125-2 and determined as a nuisance is prevented from being determined as a defect. Further, a binary logic may be performed, and for example, a differential signal value of an inspection in which a nuisance is determined may be set to 0.

The first defect determining section 181-1 determines an attribute of a defect using the same technique as in the first modified example described with reference to FIG. 1B based on the feature quantity that has been converted by the feature quantity converting section 185 and accumulated in the feature quantity storing buffer 125-2.

The above-described determination will be described using a data sheet illustrated in FIG. 15. Referring to FIG. 15, 1501 indicates a defect candidate ID that is an identifier allocated to each defect candidate. 1502 indicates an inspection ID that is an identifier allocated to each of sample inspections of multiple times. The defect candidate ID 1501 is used to associate defect candidates at the same positions which are obtained by different inspections based on coordinates 1503 of defect candidates obtained by inspections of multiple times and allocate an identifier. Further, even when the coordinates 1503 of the defect candidates are different, the defect candidates are regarded as the same defect and allocated one defect ID based on, for example, information in which a sequence of points are arranged in a line form.

In FIG. 15, 1504 indicates a defect determination feature quantity calculated based on the feature quantity accumulated in the feature quantity storing buffer 125-2 of FIG. 1C, and is typically a value obtained by dividing a difference between the inspection image and the reference image by a variation of a differential image calculated for each pixel. 1505 indicates a temporary defect determination result determined by the second defect determining section 181-2, and a determination result is output in a case in which a determination result is apparently understood such as scratch defect or a nuisance generated in an edge portion of a pattern with high intensity, and an indefinite result is output for the other cases. Further, a likelihood indicating a probability of a defect is output and indicated by a gain H. As a simple method, when a nuisance is determined, it is indicated by 0, and it is indicated by 1 otherwise. In a more advanced implementation, in the multi-dimensional feature space formed in the defect determining section 181-2, a boundary plane for identifying a specific defect and a nuisance is set to 0.5, and the likelihood is indicated by a sigmoid function having a distance from the boundary plane to the nuisance side as a parameter, and this likelihood is referred to as a "gain H."

In FIG. 15, 1506 is one which is obtained by converting an evaluation value of the defect determination feature quantity 1504 based on the gain H obtained by the defect determining section 181-2. Since it is difficult to calculate the gain H for data in which the clipped image is not accumulated, a previously set gain H0 is given, and the conversion is performed. H0 is commonly a value that is equal to or larger than 0.5 and equal to or less than 1, but since an appropriate value changes according to a parameter deciding a profile of the sigmoid function, it is preferably given as a parameter set by the user.

FIG. 2 is a diagram illustrating an exemplary configuration of an image acquiring section 110' based on the dark-field illumination as a specific example of the configuration of the image acquiring section 110 in the first embodiment and the first and second modified examples. The image acquiring section 110' includes a stage 220, a mechanical controller 230, two illumination optical systems 240-1 and 240-2 of an illumination section 240, detection optical systems (an upper detection system and an oblique detection system) 250-1 and 250-2, and image sensors 260-1 and 260-2. And the upper detection system 250-1 includes an object lens 251-1, a spatial frequency filter 252-1, an imaging lens 253-1, and an analyzer 254-1. Further, the oblique detection system 250-2 includes an object lens 251-2, a spatial frequency filter 252-2, an imaging lens 253-2, and an analyzer 254-2.

A sample 210 is an object to be inspected such as a semiconductor wafer, for example. The stage 220 is loaded with the sample 210 and able to perform movement and rotation (θ) within an XY plane and movement in a Z direction. The mechanical controller 230 is a controller that drives the stage 220. The sample 210 is obliquely irradiated with illumination light emitted from any one of the illumination optical systems 240-1 and 240-2 of the illumination section 240, scattering light from the sample 210 is formed as an image by each of the upper detection system 250-1 and the oblique detection system 250-2, and the formed optical image is received by each of the image sensors 260-1 and 260-2 and then converted into an image signal. At this time, a two-dimensional image can be obtained as a detection result by loading the sample 210 on the stage 220 of X-Y-Z-θ driving and detecting alien substance scattering light while moving the stage 220 in the horizontal direction.

A laser or a lamp may be used as an illumination light source of the two illumination optical systems 240-1 and 240-2 of the illumination section 240. Further, wavelength light of each illumination light source may short-wavelength light or broadband wavelength light (white light). When the short-wavelength light is used, in order to increase the resolution of an image to be detected (to detect a minute defect), wavelength light of an ultraviolet region (ultraviolet (UV) light) may be used. When the laser is used as a light source, in the case of a single-wavelength laser, each of the two illumination optical systems 250-1 and 250-2 of the illumination section 240 may be equipped with a device (not illustrated) for reducing coherence.

Further, in the image acquiring section 110 illustrated in FIG. 2, an epi-illumination light source 240-3 that illuminates the sample 210 through the object lens 251-1 of the upper detection system 250-1 is arranged, and a light path is changed by a folding mirror (not illustrated) at the position of a spatial filter 252-1 so that the illumination light can be incident downward. Further, by arranging a wavelength plate (not illustrated) between each of the illumination optical systems 240-1, 240-2, and 240-3 of the illumination section 240 and the sample 210, it makes possible to change the polarization state of the illumination incident on the sample 210. A rotation angle of the wavelength plate can be adjusted by a control section 270, and thus it is possible to switch the illumination polarization of each inspection condition.

Further, each of the image sensors 260-1 and 260-2 employs a time delay integration (TDI) image sensor configured such that a plurality of one-dimensional image sensors are arranged two-dimensionally, and it is possible to obtain a two-dimensional image at a relative high speed with a high degree of sensitivity by transferring a signal detected by each one-dimensional image sensor to a subsequent-stage one-dimensional image sensor in synchronization with movement of the stage 220 and adding the signals. By using a sensor of a parallel output type equipped with a plurality of output taps as the TDI image sensor, it is possible to process outputs from the sensors in parallel, and it is possible to perform high-speed detection. Further, when a backside illumination sensor is used as the image sensors 260-1 and 260-2, it is possible to increase detection efficiency to be higher than when a front side illumination sensor is used.

The detection results output from the image sensors 260-1 and 260-2 are transferred to the image storing buffers 120-1 and 120-2 and the defect candidate extracting units 130-1 and 130-2 of the defect candidate extracting section 130 via the control section 270.

Figure 3A:
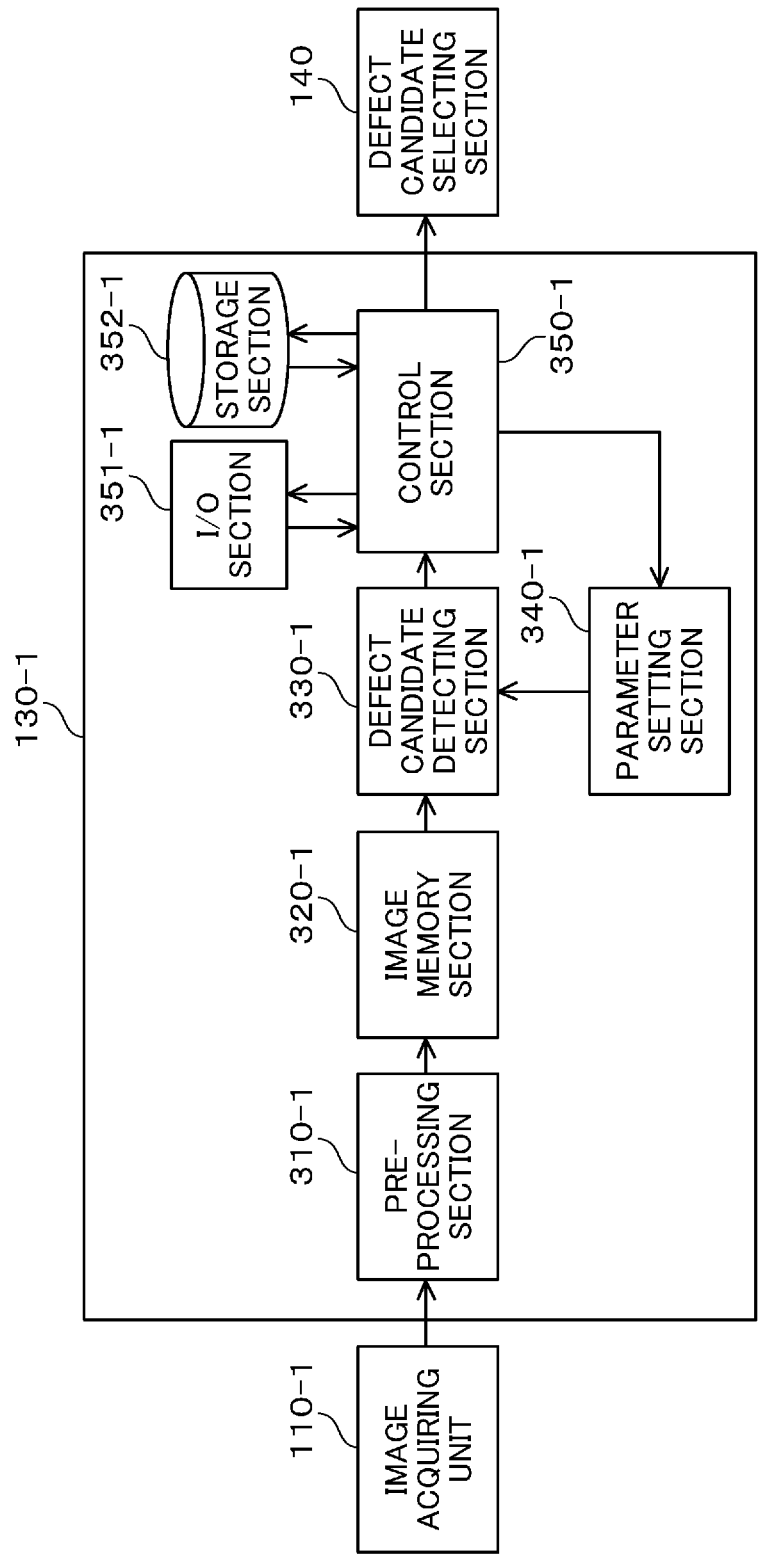
FIG. 3A is a block diagram illustrating an exemplary configuration of a defect candidate extracting section in the defect inspection devices according to the first embodiment and the first and second modified examples of the present invention.

FIG. 3A is a diagram illustrating an exemplary configuration of the defect candidate extracting unit 130-1 of the defect candidate extracting section 130 in the first embodiment and the first and second modified examples. The defect candidate extracting unit 130-1 includes a pre-processing section 310-1, an image memory section 320-1, a defect candidate detecting section 330-1, a parameter setting section 340-1, a control section 350-1, a storage section 352-1, and an input/output (I/O) section 351-1. The defect candidate extracting unit 130-2 has the same configuration.

First, the pre-processing section 310-1 performs image correction such as shading correction, dark level correction, and bit compression on the image data input from the image acquiring section 110-1, divides the image data into images having a size of a certain unit, and stores the divided images in the image memory section 320-1. A digital signal of an image (hereinafter, referred to as a "reference image") of a region corresponding to an image (hereinafter, referred to as a "detection image") of an inspected region stored in the image memory 320-1 is read out.

Here, an image of a neighboring chip or an ideal image having no defect in an image which is created from a plurality of neighboring chip images may be used as the reference image. Further, a corrective amount for adjusting the position in a plurality of neighboring chip defect candidate detecting sections 330-1 is calculated, an alignment between the detection image and the reference image is performed using the calculated position corrective amount, and a pixel serving as a deviation amount on the feature space using a feature quantity of a corresponding pixel is output as a defect candidate.

The parameter setting section 340-1 sets inspection parameters such as a type and a threshold of a feature quantity, which are input from the outside, in extracting defect candidate, and provides the set inspection parameters to the defect candidate detecting section 330-1. The defect candidate detecting section 330-1 outputs, for example, the image or the feature quantity of the extracted defect candidate to the defect candidate selecting section 140 via the control section 350-1. The control section 350-1 is equipped with a CPU that performs various kinds of control and connected with the I/O section 351-1 including a display device that displays detected defect information and an input device that receives the inspection parameters (the type and the threshold of the feature quantity) changed by the user and the storage section 352-1 that stores, for example, the feature quantity and the image of the detected defect candidate.

Here, the control section 150 described with reference to FIGS. 1A to 1C, the control section 270 described with reference to FIG. 2, and the control sections 350-1 and 350-2 described with reference to FIG. 3A may be configured with the same control unit or may be configured with different control units and connected to one another.

A typical feature quantity used to extract a defect candidate is now described. Here, when coordinates in a die are indicated by (x, y), an identifier of a detection image acquisition condition is indicated by k, a difference between an inspection image and a reference image is indicated by Diff, differential filter strength of the reference image at a defect candidate position is indicated by edge, a brightness variation in coordinates in the same die is indicated by Δdie, a pattern attribute at the position of the defect candidate is indicated by id(x, y), and a variation in the difference between the inspection image and the reference image in the pattern portion is indicated by Δcateg, one satisfying (Formula 1) as a basic form is extracted as the defect candidate.

[Math 1]

$$\mathrm{Diff}(k,x,y)^2 > A(k)\mathrm{edge}(k,x,y)^2, B(k)\Delta\mathrm{Die}(k,x,y)^2, C(k)\Delta\mathrm{categ}(k,id(x,y),x,y)^2 \quad \text{(Formula 1)}$$

A(k), B(k), and C(k) are parameters set for each inspection image acquisition condition, and the values are set to different values based on the defect candidate remaining in 120 and the defect candidate remaining in 125, and as will be described later, A(k), B(k), and C(k) may be changed according to each coordinates or may be changed according to each defect type to be assumed. When A, B, and C are changed according to each defect type, a boundary plane having the highest sensitivity is assumed to be selected in the multi-dimensional space.

FIG. 3B is an explanatory diagram of a deviation amount detecting method of the defect candidate detecting section. (Formula 2) is a transformation of (Formula 1), and 360 indicates a scatter diagram of the state of (Formula 2). 361 and 362 indicate DOIs, and 363 that is the remaining distribution indicates a nuisance.

[Math 2]

$$1 > A(k)\frac{edge(k, x, y)^2}{Diff(k, x, y)^2} + \qquad \text{(Formula 2)}$$
$$B(k)\frac{\Delta Die(k, x, y)^2}{Diff(k, x, y)^2} + C(k)\frac{\Delta categ(k, id(x, y), x, y)^2}{Diff(k, x, y)^2}$$

Here, as a typical example, a determination formula is described based on the sum of values obtained by squaring a feature quantity, but a linear form may be used as it is without squaring a feature quantity.

A next formula, that is, (Formula 3) is obtained by performing normalization based on the threshold of (Formula 1) and multiplying a gain G(k) of each detection condition, and indicates a determination formula in a plurality of detection conditions.

[Math 3]

$$\sum_k G(k)\frac{Diff(k, x, y)^2}{A(k)edge(k, x, y)^2 + B(k)\Delta Die(k, x, y)^2 + C(k)\Delta categ(k, id(x, y), x, y)^2} \qquad \text{(Formula 3)}$$

In (Formula 3), it is difficult to perform an accurate operation unless the defect candidate is selected by (Formula 2). In this regard, A, B, and C in (Formula 2) are set small values for defect detections based on only one general image. Here, when A, B, and C are set to very small values, the number of defect candidates is too large, and there is a problem in that a large buffer is necessary, or a processing time at a subsequent stage is drastically increased. Since the present inspection method is an inspection method in which inspections of N times are integrated, a mechanism in which a position at which a defect candidate is selected is input to the defect candidate detecting section in advance, and a small threshold is exceptionally set within a deviation amount permissible value range among a plurality of inspections, or a pixel that is most likely to be a defect is output as a defect candidate is provided, and the parameters A, B, and C need not be extremely decreased.

Figure 4:
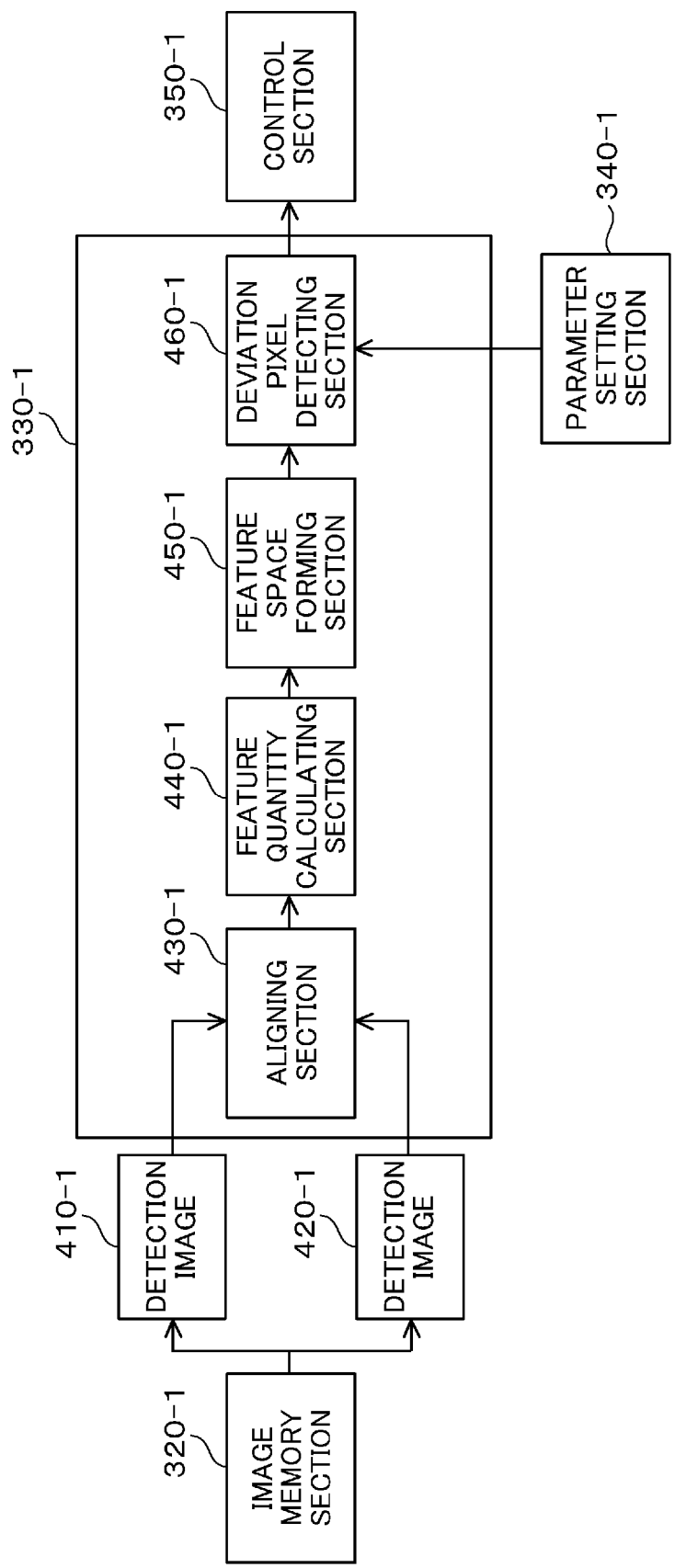
FIG. 4 is a block diagram illustrating an exemplary configuration of a defect candidate detecting section in the defect inspection devices according to the first embodiment and the first and second modified examples of the present invention.

FIG. 4 illustrates an exemplary configuration of the defect candidate detecting section 330-1 in the first embodiment and the first and second modified examples. The defect candidate detecting section 330-1 includes an aligning section 430-1, a feature quantity calculating section 440-1, a feature space forming section 450-1, and a deviation pixel detecting section 460-1. The aligning section 430-1 detects and corrects a misalignment between a detection image 410-1 and a reference image 420-1 input from the image memory section 320-1. The feature quantity calculating section 440-1 calculates a feature quantity from corresponding pixels of the detection image 410-1 and the reference image 420-1 in which the misalignment has been corrected by the aligning section 430-1. Here, the feature quantity to be calculated is assumed to include a brightness difference between the detection image 410-1 and the reference image 420-1, the sum of brightness differences in a certain region, or a variation in a brightness difference in a certain region.

The feature space forming section 450-1 forms a feature space corresponding to 360 of FIG. 3B based on a feature quantity that is arbitrarily selected. The deviation pixel detecting section 460-1 outputs a pixel located at a deviated position in the feature space as a defect candidate. The feature space forming section 450-1 may perform normalization based on, for example, a variation of each defect candidate. Here, as a criterion for determining a defect candidate, in addition to (Formulas 1) and (Formula 2), for example, a variation of a data point in the feature space or a distance from a center of gravity of a data point may be used. At this time, a determination criterion may be decided using the parameter input from the parameter setting section 340-1.

Figure 5A:
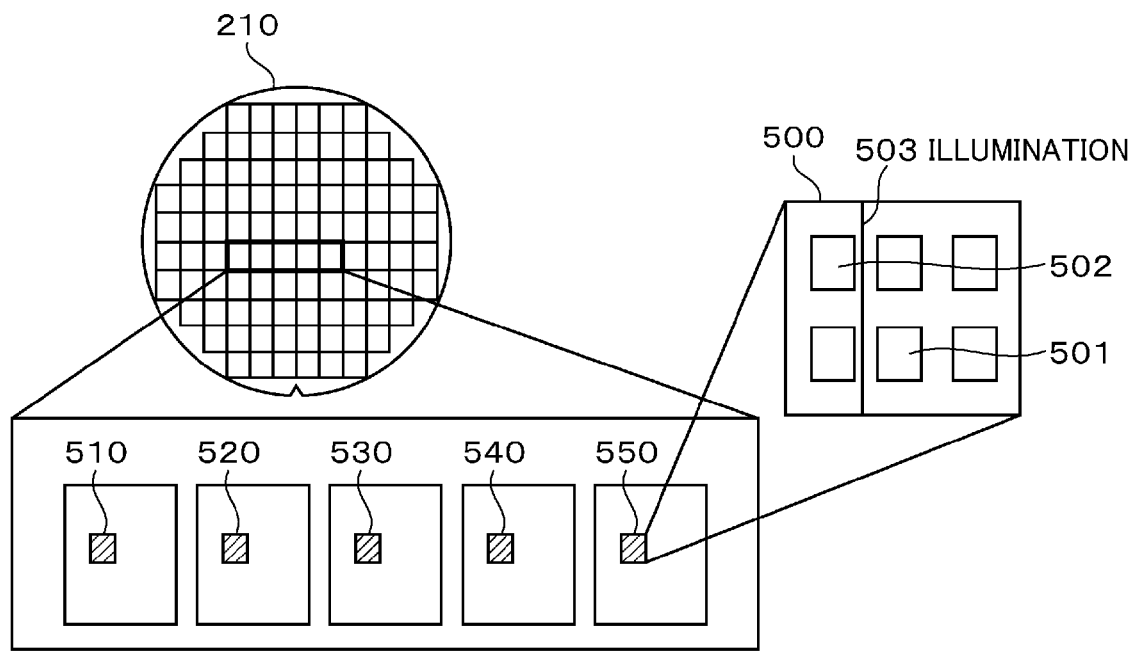
FIG. 5A is a plan view of a semiconductor wafer and an enlarged view of a plurality of dies illustrating a configuration of a die of a semiconductor wafer serving as an inspection target in the defect inspection devices according to the first embodiment and the first and second modified examples of the present invention.
Figure 5B:
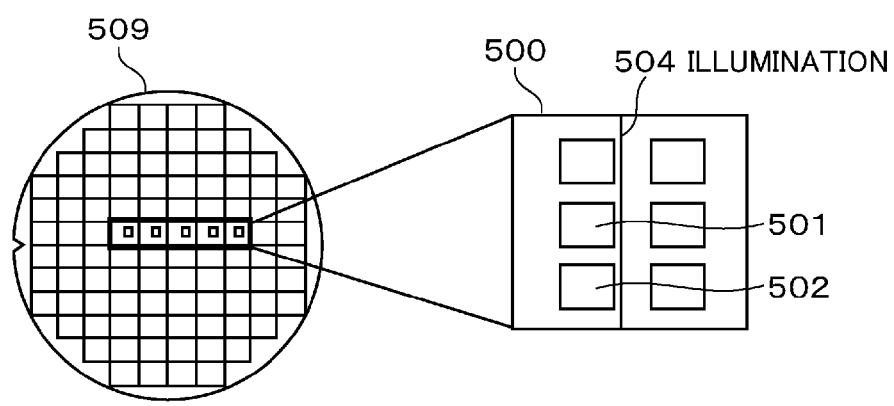
FIG. 5B is a plan view of a semiconductor wafer and an enlarged view of a plurality of dies illustrating a configuration of a die of a semiconductor wafer serving as an inspection target in the defect inspection devices according to the first embodiment and the first and second modified examples of the present invention.

FIGS. 5A and 5B are diagrams illustrating an exemplary configuration of a chip serving as an inspection target in the defect inspection devices according to the first embodiment and the first and second modified examples of the present invention, that is, diagrams for describing the defect candidate detection by the defect candidate detecting section 330-1. The sample (which is also referred to as a "semiconductor wafer" or a "wafer") 210 serving as the inspection target includes a plurality of chips 500 having the same patterns which are regularly arranged, and each of the chip 500 includes a memory mat section 501 and a peripheral circuit section 502. The control section 270 continuously moves the semiconductor wafer 210 serving as the sample through the stage 220, and illuminates 503 and 504 sequentially in synchronization with the continuous movement, images of chips are acquired by the image sensors 260-1 and 260-2, digital image signals of regions 510, 520, 540, and 550 are set as a reference image for the same position of chips that are regularly arranged in a detection image, for example, a region 530 of the detection image of FIG. 5A, a comparison with a corresponding pixel of the reference image or another pixel in the detection image is performed, and a pixel having a large difference is detected as a defect candidate. Here, a sample 509 of FIG. 5B is one in which the wafer of the sample 210 of FIG. 5A is rotated by 90 degrees.

In FIGS. 5A and 5B, a pattern of a region of the peripheral circuit section 502 is exposed as a pattern that is periodic in a longitudinal direction of an illumination 503 by the illumination 503, and a pattern of a region 501 is exposed as a pattern that is periodic in a longitudinal direction of an illumination direction by an illumination 504. The scattered light from the periodic patterns can be cut by the spatial frequency filters 252-1 and 252-2 illustrated in FIG. 2, but a scattered light from a pattern that is periodic in a transverse direction of the illumination can hardly be cut by the spatial frequency filter. As described above, since a region in which a noise can be cut changes according to a combination of the illumination direction and the spatial frequency filter, an inspection in which an image acquisition condition is changed multiple times is necessary.

Figure 6A:
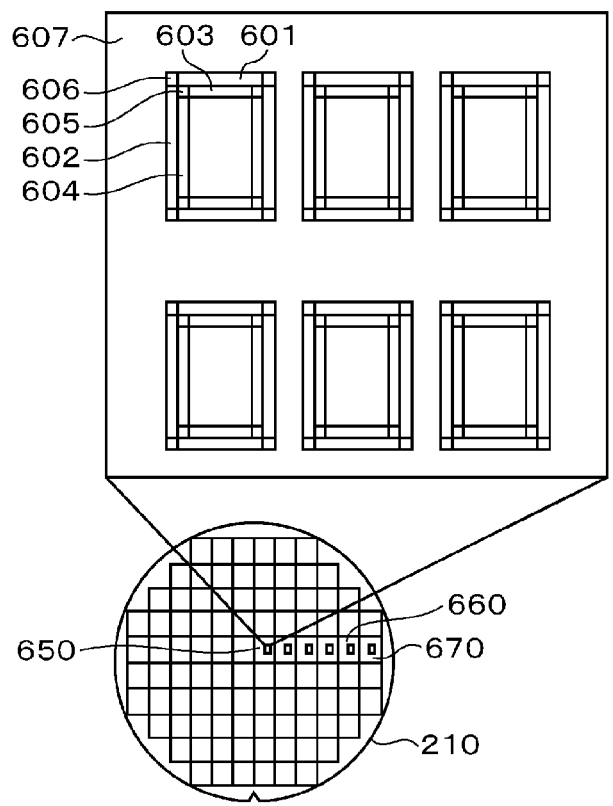
FIG. 6A is a plan view of a semiconductor wafer and an enlarged view of a plurality of dies illustrating an example in which an inside region of a die formed in a semiconductor wafer serving as an inspection target is divided in the defect inspection devices according to the first embodiment and the first and second modified examples of the present invention.
Figure 6B:
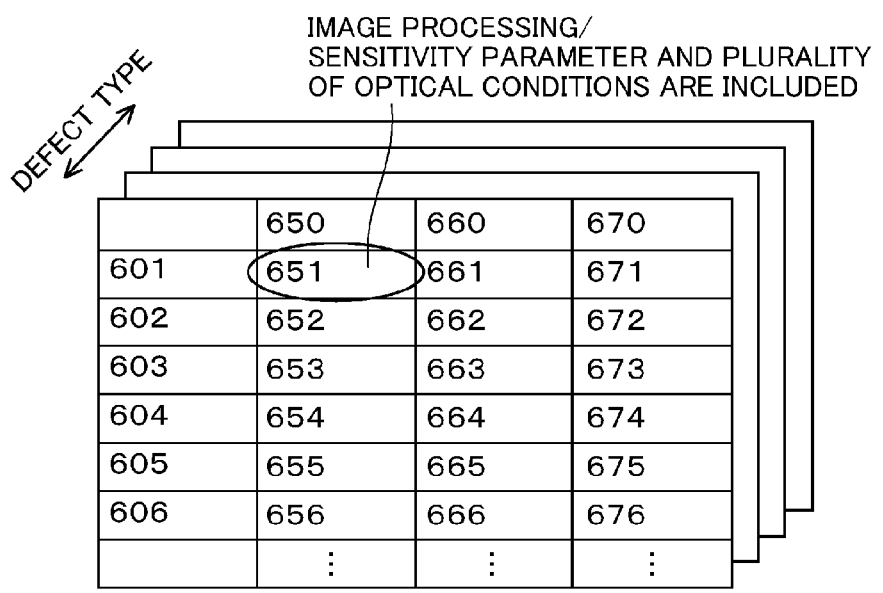
FIG. 6B illustrates an example of a list of processing conditions in which an inside region of a die formed in a semiconductor wafer serving as an inspection target is divided, and an inspection condition of each divided region is summarized in the defect inspection devices according to the first embodiment and the first and second modified examples of the present invention.

FIG. 6A is a pattern obtained by performing region division on the patterns illustrated in FIGS. 5A and 5B. 601 to 606 indicate regions to which an inspection condition is set. As described above, when the inspection is performed using the image acquiring section 110 having the configuration illustrated in FIG. 2, a noise appearance form changes according a region based on a relation between a pattern to be inspected and an illumination. Thus, the defect determination criterion is changed by changing the feature space formed by the feature space forming section 450-1 for each region. Further, since a noise occurrence state and a defect occurrence state of the sample 210 change according to a center 650, a periphery 660, and an edge 670 of the sample 210, a feature quantity space is set such that each region is combined with regions 601 to 607 in a die and divided into regions 651 to 656, 661 to 666, and 671 to 676 as illustrated in FIG. 6B. Further, since an image acquisition condition for exposure and a detection priority of the user differ according to each defect type, the defect determination criterion differing according to each defect type is used.

The determination criterion includes a criterion for the following evaluation values:

(a) an evaluation value of the defect candidate detecting section 330-1 illustrated in FIG. 3A;

(b) an evaluation value for storing the clipped image in the buffer 121 in the defect candidate selecting section 140 of FIG. 1B;

(c) an evaluation value for storing the feature quantity data in the feature quantity storing buffer 125-2;

(d) an evaluation value for separating a defect from a nuisance in the first defect determining section 180-1; and (e) an evaluation value for separating a defect from a nuisance in the second defect determining section 180-2.

Figure 7A:
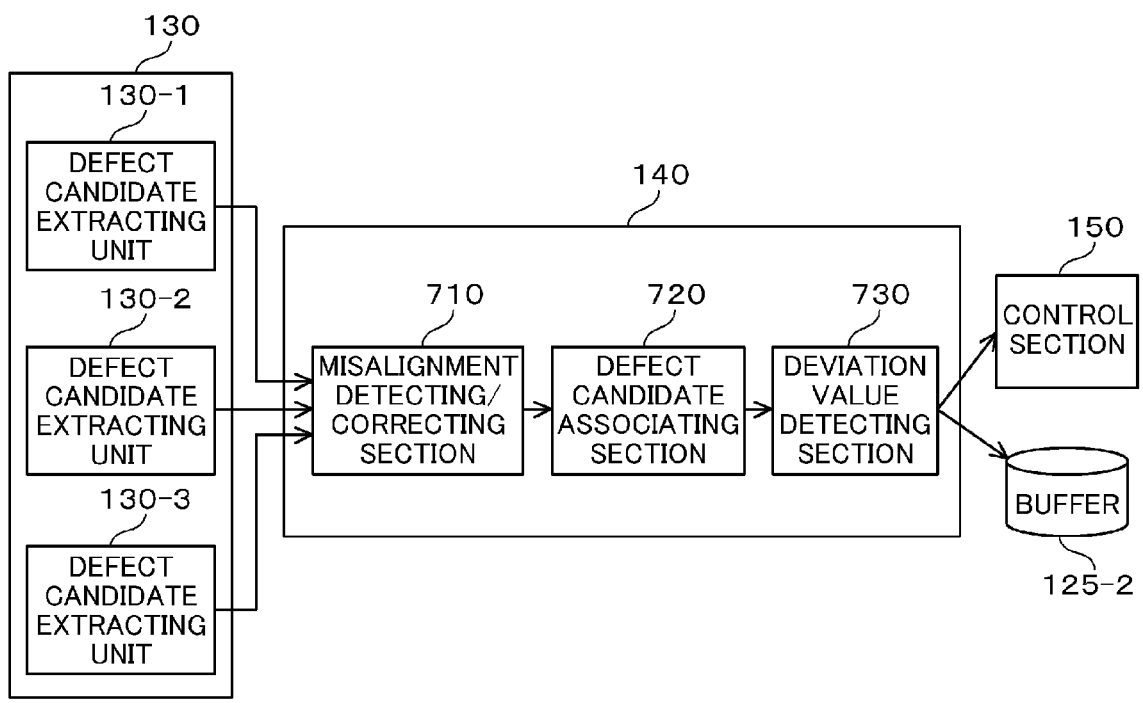
FIG. 7A is a block diagram illustrating a configuration of a defect candidate selecting section in the defect inspection devices according to the first and second modified examples of the first embodiment of the present invention.

FIG. 7A is a diagram illustrating an exemplary configuration of the defect candidate selecting section 140 in the defect inspection devices according to the first and second modified examples of the first embodiment of the present invention. The defect candidate selecting section 140 includes a misalignment detecting/correcting section 710, a defect candidate associating section 720, and a deviation amount detecting section 730. The misalignment detecting/correcting section 710 receives images and feature quantities of a plurality of defect candidates and a detection position on a wafer from the defect candidate extracting sections 130-1, 130-2, and 130-3, and detects and corrects a misalignment of wafer coordinates in each defect candidate.

The defect candidate associating section 720 performs grouping of a defect candidate group from images acquired at the same position in different conditions by associating the defect candidates whose detection position has been corrected by the misalignment detecting/correcting section 710. The associating is performed, for example, by a method of determining whether or not the defect candidates overlap within a predetermined range on the wafer coordinates. When the defect candidates do not overlap within the range, it is desirable to access evaluation data of the defect candidate extracting units 130-1, 130-2, and 130-3 of the defect candidate extracting section 130 from the defect candidate associating section 720 and acquire the feature quantity data. Further, in order to prevent the system from being complicated, the deviation amount detecting section 730 may be executed by excluding an image acquisition condition in which it was difficult to detect a specific defect candidate. Further, the same defect candidate associating section as the defect candidate associating section 720 is incorporated into the defect determining section 180-1 (181-1) as well so that the feature quantity can be collected from the same defect candidate in inspections of multiple times.

The deviation amount detecting section 730 sets a threshold to the defect candidate associated by the defect candidate associating section 720, detects a defect candidate located at a deviated position in the feature space, and outputs, for example, the feature quantity or the detection position of the defect candidate to the control section 150. At this time, typically, one satisfying the determination formula illustrated in (Formula 3) is determined as a defect. Each element of the feature vector in the multi-dimensional space is typically represented by (Formula 4).

[Math 4]

$$\sqrt{\frac{G(k)Diff(k,x,y)^2}{A(k)edge(k,x,y)^2+B(k)\Delta Die(k,x,y)^2+C(k)\Delta categ(k,id(x,y),x,y)^2}} \quad \text{(Formula 4)}$$

When there is no defect candidate in a specific image while grouping the defect candidates at the same coordinates, it is difficult to accurately solve (Formula 3), but a feature quantity of an image k in which it was difficult to detect a defect candidate is G(k) or less from a relation between (Formula 1) and (Formula 3). G(k) can be decreased by decreasing a denominator of (Formula 3), that is, the right side of (Formula 1).

Generally, the right side of (Formula 1) is set to X times of a standard deviation of Diff serving as a defect signal value, and a feature of a position in which no defect candidate was detected can be set to a value of $G(k)^{0.5}/X$. As the defect signal of the feature quantity is normalized using the defect detection threshold as described above, it is possible to estimate a feature quantity without a large error even when it is difficult to detect a defect candidate. Further, since G(k) decreases as the right side of (Formula 1) decreases, that is, as X decreases, an error does not significantly increase although a feature of a potion in which there was no defect candidate is set to 0. Here, (Formula 1), (Formula 2), and (Formula 3) represent square form examples, but even when (Formula 1), (Formula 2), and (Formula 3) are linear formulas, it is possible to estimate a feature quantity similarly if it is represented in a form in which the defect signal Diff is normalized by a threshold for detecting a defect candidate or if a threshold is normalized by the defect signal Diff.

In the table illustrated in FIG. 6B, typically, the parameters A(k), B(k), C(k), and G(k) in (Formula 3) are stored as a parameter for separating each defect type from a nuisance. When (Formula 4) is satisfied in any one of the defect types, it is temporarily determined as a defect candidate of the defect type. The deviation amount detecting section 730 performs an output to the control section 150 and the feature quantity storing buffer 125-2, and this is implemented such that the values of the parameters A(k), B(k), and C(k) are set for the control section 150 and the feature quantity storing buffer 125-2.

The control section 150 sets A(k), B(k), C(k), and G(k) to a large value for the parameter that is output to the feature quantity storing buffer 125-2, and thus the number of clipped images stored in the buffers 120-1, 120-2, and 120-3 of the buffer 120 is typically decreased to be smaller than the number of feature quantities stored in the feature quantity storing buffer 125-2. Further, an upper limit may be set to the number of defect candidates stored in each buffer, and when the upper limit is exceeded, a defect candidate may be output to the control section 150 from a defect significantly deviated from the boundary plane of (Formula 3). Furthermore, (Formulas 2) and (Formula 3) are formulated in a form in which each feature quantity is squared, but the present configuration can be implemented in a form in which each feature quantity is not squared, another modified form, and even an increase or decrease in the number of feature quantities.

Figure 7B:
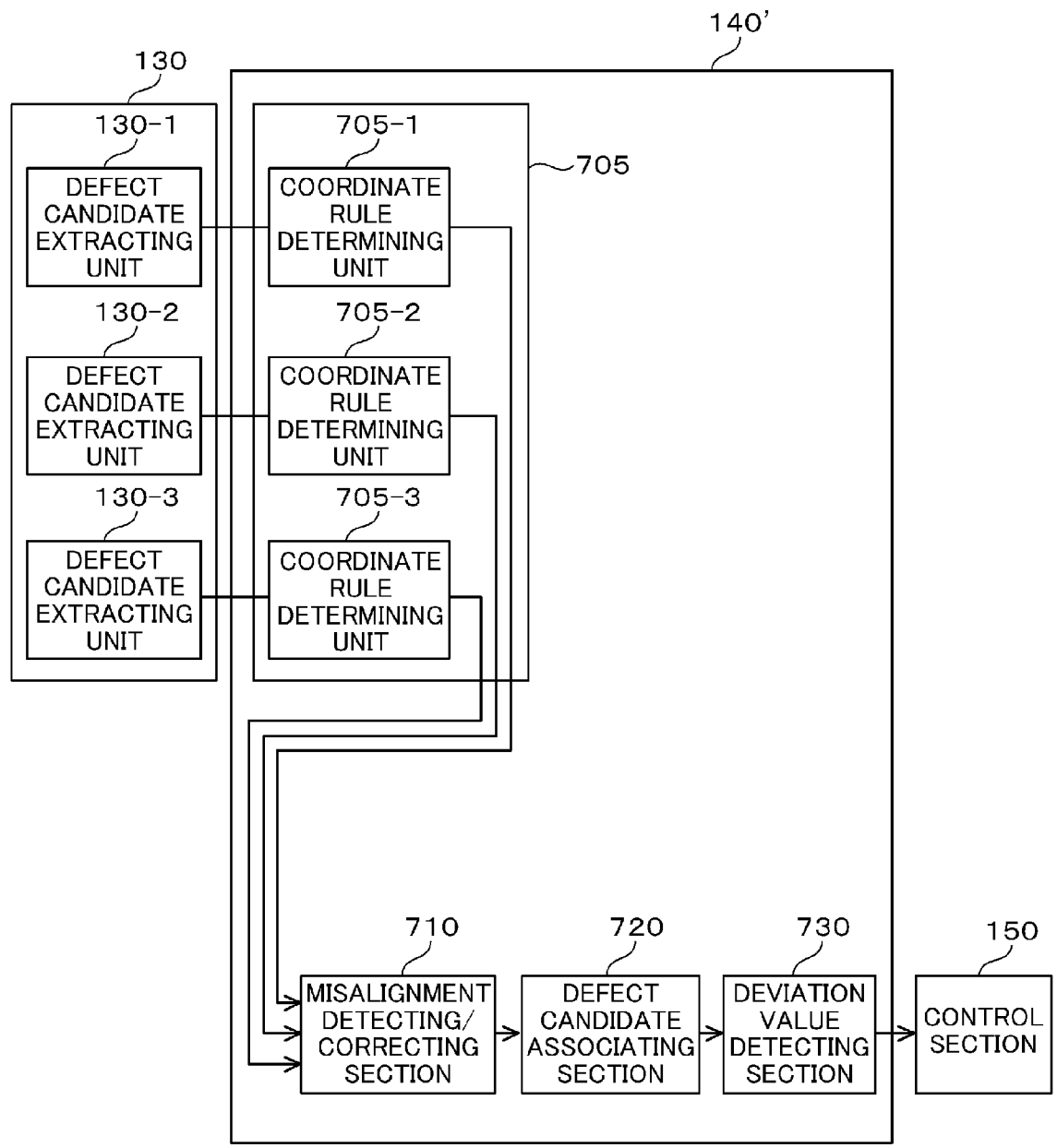
FIG. 7B is a block diagram illustrating a configuration of a modified example of a defect candidate selecting section in the defect inspection devices according to the first embodiment and the first and second modified examples of the present invention.

FIG. 7B illustrates an embodiment in which the defect candidate selecting section 140 described with reference to FIG. 7A is modified. As the defect candidate selecting section 140' of FIG. 7B, a coordinate rule determining section 705 including coordinate rule determining unit 705-1, 705-2, and 705-3 that perform nuisance removal or defect extraction on coordinates of the defect candidates output from the defect candidate extracting units 130-1, 130-2, and 130-3 of the defect candidate extracting section 130 based on regularity of the coordinates is added to the defect candidate selecting section 140 described with reference to FIG. 7A.

Figure 7C:
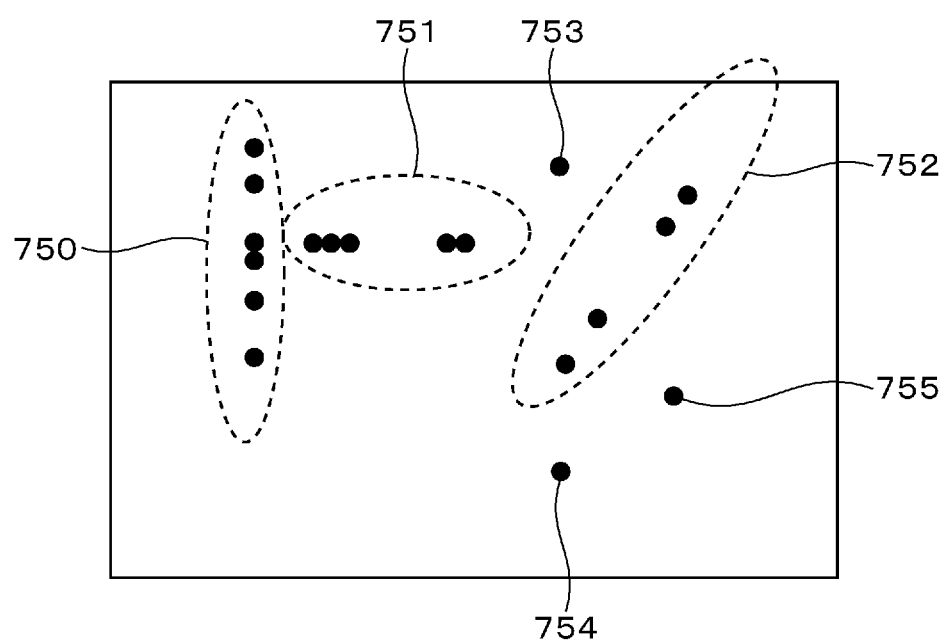
FIG. 7C is a defect candidate distribution diagram for describing an example of a coordinate determination rule used to determine regularity of coordinates of a detected defect in the defect inspection devices according to the first embodiment and the first and second modified examples of the present invention.

FIG. 7C is a defect candidate distribution diagram illustrating an example of a coordinates determination rule for distinguishing a scratch and a nuisance in a circuit pattern boundary portion. For example, when a straight line detection algorithm such as Hough transformation is applied to coordinates of a defect candidate, it is possible from a sequence of defect candidates to distinguish dot sequences 750, 751, and 752 that are arranged in a straight line form and surrounded by a dotted line from a group of remaining points.

As the causes of defect coordinates arranged in a straight line form, two cases, that is, a case in which defects have actually occurred in a line form and a case in which a boundary portion of a circuit pattern having a large brightness variation has been detected as a nuisance are considered. In the case of a nuisance, a line is generally often arranged in a horizontal or vertical direction with respect to a circuit pattern sequence, whereas in the case of a scratch defect, it is unlikely to occur in a specific direction. Thus, the dot sequences 750 and 751 arranged horizontally or vertically in the straight line form have a high possibility of a nuisance, and the dot sequence 752 arranged obliquely in the straight line form has a high possibility of a scratch defect. Further, since a scratch defect is a shape feature in which a dot sequence is continued, it can be distinguished from a noise or a nuisance, but there are cases in which it is very difficult to distinguish it from a noise or a nuisance based on only a point of each defect candidate. Thus, a defect candidate arranged in the horizontal or vertical direction with respect to the circuit pattern arranged vertically or horizontally in the straight line form such as the dot sequence 750 or 751 is determined as a nuisance in advance, and a dot sequence arranged in a direction other than the horizontal and vertical directions such as the dot sequence 752 that is arranged obliquely in the straight line form is determined as a scratch defect in advance.

The defect candidate group arranged in the straight line form is grouped into one defect candidate, the feature quantities are integrated, and a starting point and an ending point thereof are transferred to the deviation amount detecting section 730 at the subsequent stage. As an integration method, a difference in an integrated feature quantity between the inspection image and the reference image may become a sum of a dot sequence (a defect candidate group) arranged in the straight line form or may more preferably become the square root of the sum of the squares. The deviation amount detecting section 730 determines data of the integrated defect candidates with data of defect candidates that are not arranged in the straight line form such as points 753, 754, and 755. A defect candidate group determined as a nuisance is excluded from a subsequent process.

In the configuration illustrated in FIG. 7B, there is described that the coordinate rule determining section 705 performs the coordinate rule determination independently from the coordinates of the defect candidates extracted by the defect extracting unit 130-1, 130-2, and 130-3 of the defect candidate extracting section 130, but the coordinates output from the defect candidate extracting units 130-1 to 130-3 of the defect candidate extracting section 130 behind the defect candidate associating section 720 may be merged, and thereafter the coordinate rule determination may be performed.

The defect determination concept of the defect determining section 180 according to the first embodiment and the first defect determining section 180-1 or the first defect determining section 181-1 according to the first and second modified examples will be described with reference to a three-dimensional (3D) feature quantity space graph having first to third conditions as axes illustrated in FIG. 8A. The defect determining section 180 or either of the first defect determining section 180-1 and the first defect determining section 181-1 performs the defect determination based on the defect candidates accumulated in the feature quantity storing buffer 125-2. The defect determining section 180 or either of the first defect determining section 180-1 and the first defect determining section 181-1 has the same configuration as the defect candidate selecting section 140 illustrated in FIG. 7A or FIG. 7B. Here, since the defect determining section 180 or either of the first defect determining section 180-1 and the first defect determining section 181-1 performs the determination on the defect candidates accumulated as inspection results of multiple times, the dimension number of the feature space is increased, and the inspection is sequentially performed.

Thus, in the defect candidate associating section 720, when there was no defect candidate at the same coordinates in image acquisition of different conditions, it is possible to access the evaluation data of the defect candidate extracting section 130 and acquire the information, but it is difficult to perform this through the defect determining section 180 or either of the first defect determining section 180-1 and the first defect determining section 181-1. Thus, in a state in which there is no defect candidate, the feature quantity indicated by (Formula 3) is calculated, and the defect determination is performed. Here, for the feature quantity, for convenience of description, only the 3D feature space based on the feature quantities of the defect candidates stored in the feature quantity storing buffer 125-2 in which three inspection results are accumulated is illustrated in FIG. 8A, but typically, when processing is performed in the configuration of FIG. 1A by inspections of N times, dimensions of 3N are actually given. Coordinates of each dimension is represented by (Formula 5).

[Math 5]

$$\left\{ \begin{array}{c} \frac{G(k1)Diff(k1, x, y)^2}{A(k1)edge(k1, x, y)^2 + B(k)\Delta Die(k1, x, y)^2 + C(k)\Delta categ(k1, id(x, y), x, y)^2} \\ \frac{G(k2)Diff(k2, x, y)^2}{A(k2)edge(k2, x, y)^2 + B(k)\Delta Die(k2, x, y)^2 + C(k)\Delta categ(k1, id(x, y), x, y)^2} \\ \frac{G(k3)Diff(k3, x, y)^2}{A(k3)edge(k3, x, y)^2 + B(k)\Delta Die(k3, x, y)^2 + C(k)\Delta categ(k3, id(x, y), x, y)^2} \end{array} \right\}$$ (Formula 5)

Defects detected only in some image acquisition conditions among defect candidates whose threshold of a single defect is higher than thresholds 830-1, 830-2, and 830-3 by the defect candidate extracting units 130-1, 130-2, and 130-3 of the defect candidate extracting section 130 are defects 810-1 and 810-2. On the other hand, similarly to the general defect candidate extracting units 130-1, 130-2, and 130-3, the defect determining section 180 or either of the first defect determining section 180-1 and the defect determining section 181-1 sets a certain threshold 850 to a distance from an original point of the feature space formed in a plurality of detection conditions in addition to a threshold on a certain image, and determines a deviation amount using this threshold as well. In other words, deviated defect candidate deviated from the threshold with respect to the original point is assumed to be a deviation amount (a defect candidate surrounded by ○ in FIG. 8A).

Further, a logical determination method may be similarly employed in addition to the continuous boundary plane such as the threshold 850. For example, a threshold indicating the threshold 830-3 is set to the second image acquisition condition (the second condition in FIG. 8A), and a setting is performed so that a logical operation can be performed based on the strength of the defect candidate on the boundary plane set to have the strength that is stronger than the boundary plane of the threshold 850 serving as a threshold of a common defect or the strength that is stronger than the threshold 830-3. Further, a fuzzy logic may be performed as the logical operation. In this case, when a defect is detected only in a specific image acquisition condition, there is a problem in that it is difficult to accurately calculate a distance from the original point in the feature space.

A defect that is detected only in a specific condition such as the defects 810-2 and 810-3 in FIG. 8A will be described with reference to FIGS. 8B to 8F. In FIG. 8B, 1801 indicates a sample pattern, and 1802 indicates a defect. In the case of the optical inspection device illustrated in FIG. 2, it is possible to switch polarized light of an illumination and then perform illumination, but in S-polarized light or TE-polarized light in which a direction of an electric field is orthogonal to a groove of the pattern 1801, the illumination reaches the inside of the groove, and thus it is easy to detect a defect, whereas in TM-polarized light or P-polarized orthogonal thereto, the illumination does not reach the inside of the groove, and thus it is difficult to detect a defect.

Figure 8A:
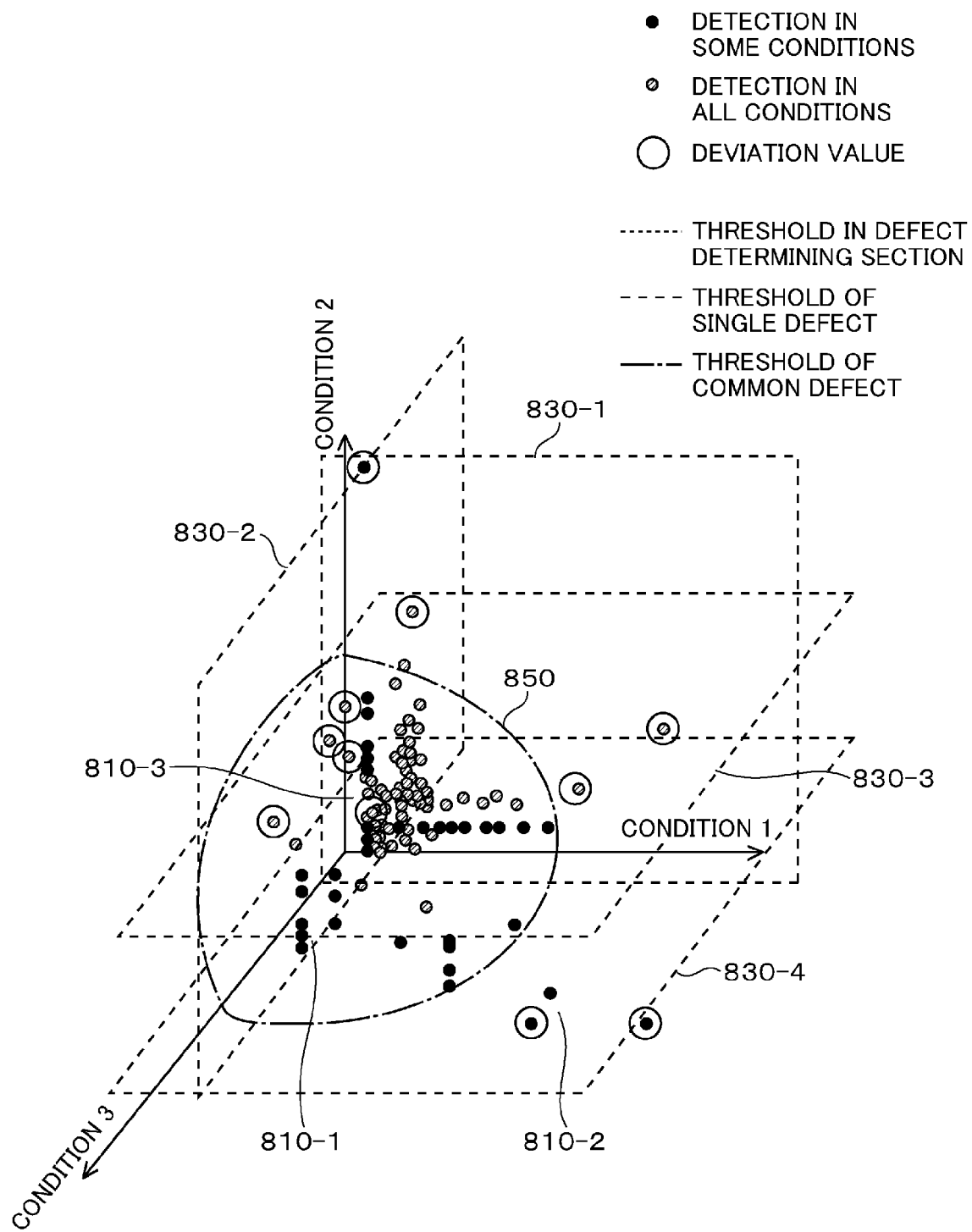
FIG. 8A is a three-dimensional graph illustrating an example of a feature space of a defect determining section in the defect inspection devices according to the first embodiment and the first and second modified examples of the present invention.
Figure 8B:
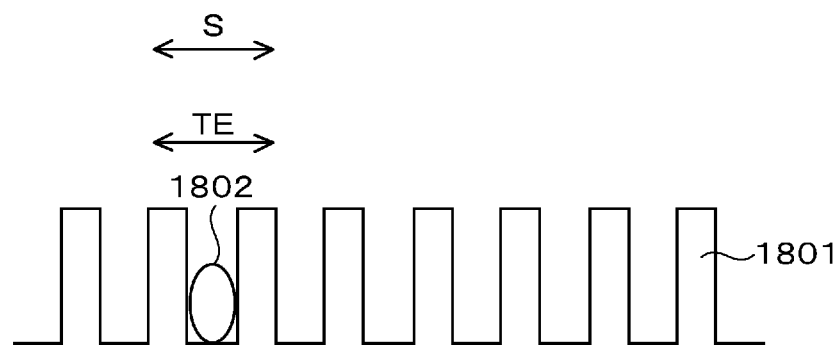
FIG. 8B is a front view of an inspection target pattern illustrating an example in which a defect is detected only in a specific condition.
Figure 8C:
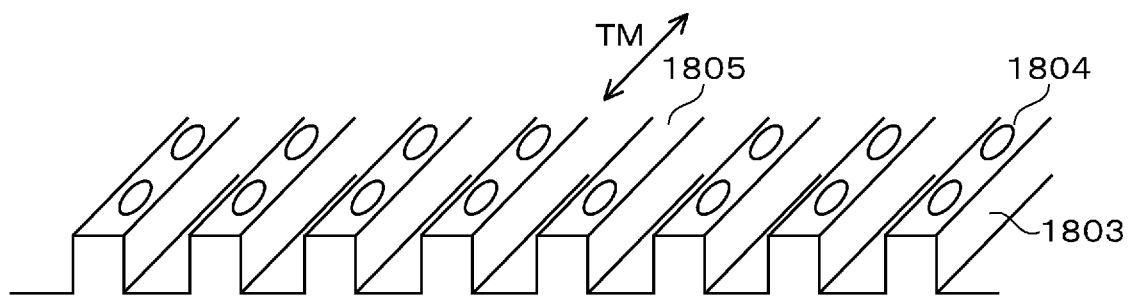
FIG. 8C is a perspective view of an inspection target pattern illustrating an example in which a defect is detected only in a specific condition.
Figure 8D:
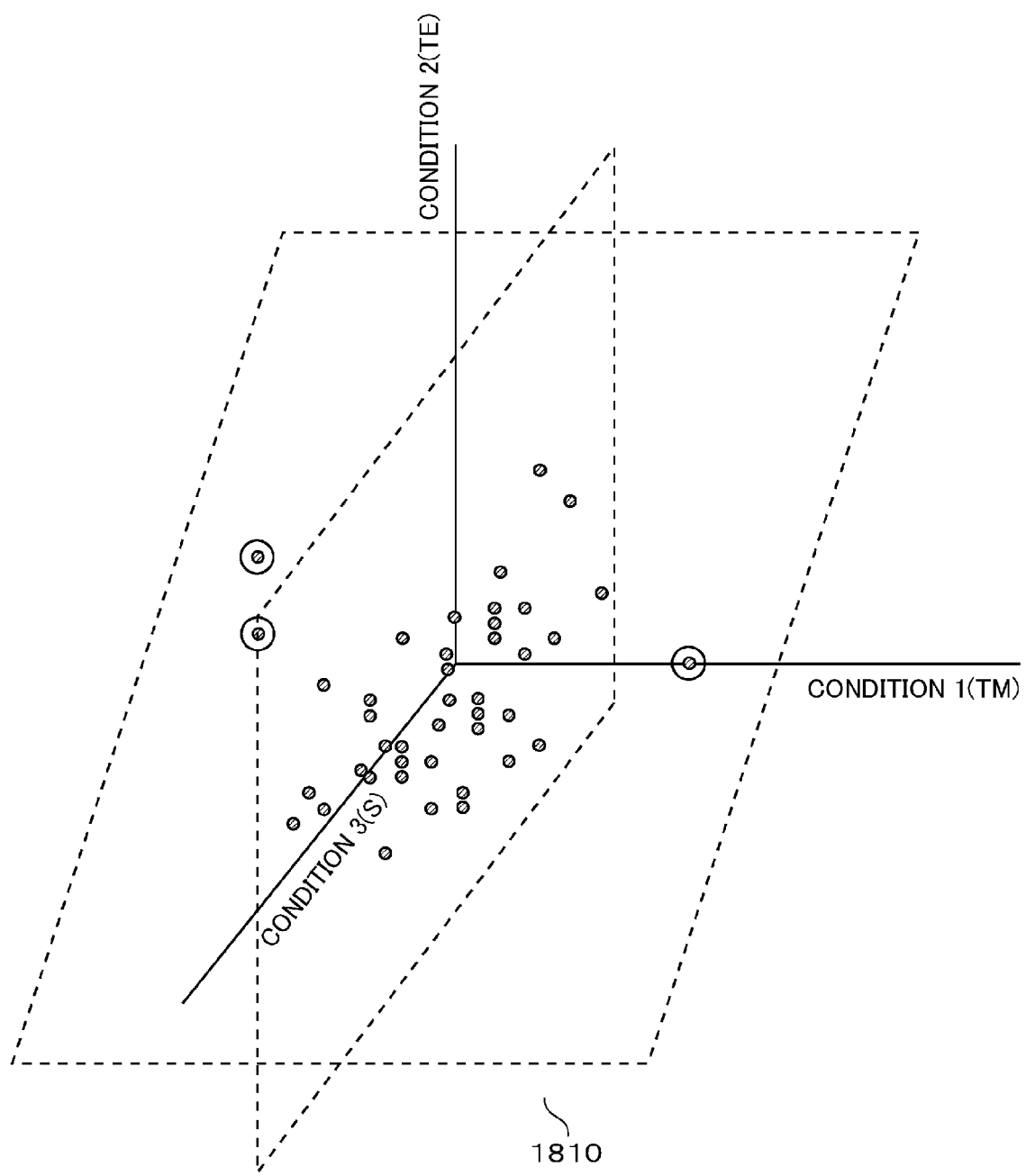
FIG. 8D is a graph in which a difference between an inspection image and a reference image is plotted in a three-dimensional space configured by respective illumination conditions.

FIG. 8C illustrates a non-opening defect 1805 occurring in a hole formed on a pattern such as 1804 in a pattern 1803. In the TE-polarized light, light reaches up to the bottom of the groove, whereas a large noise tends to be detected due to roughness of a groove portion. As a result, the non-opening defect 1805 tends to be exposed as a defect only by the TM-polarized light in which light does not reach up to the bottom of the groove. A plane 1810 surrounded by a dotted line in a 3D space of FIG. 8D indicates a difference between each illumination condition and a defect signal, that is, difference between the inspection image and the reference image, but due to the above-mentioned nature, a defect is revealed only in a specific condition. When the boundary planes 830-1 to 830-4 illustrated in FIG. 8A are set for each defect type using this nature, it is possible to set sensitivity for each defect type, and it is possible to suppress detection sensitivity of an unnecessary defect and reduce the number of detected nuisances.

Figure 8E:
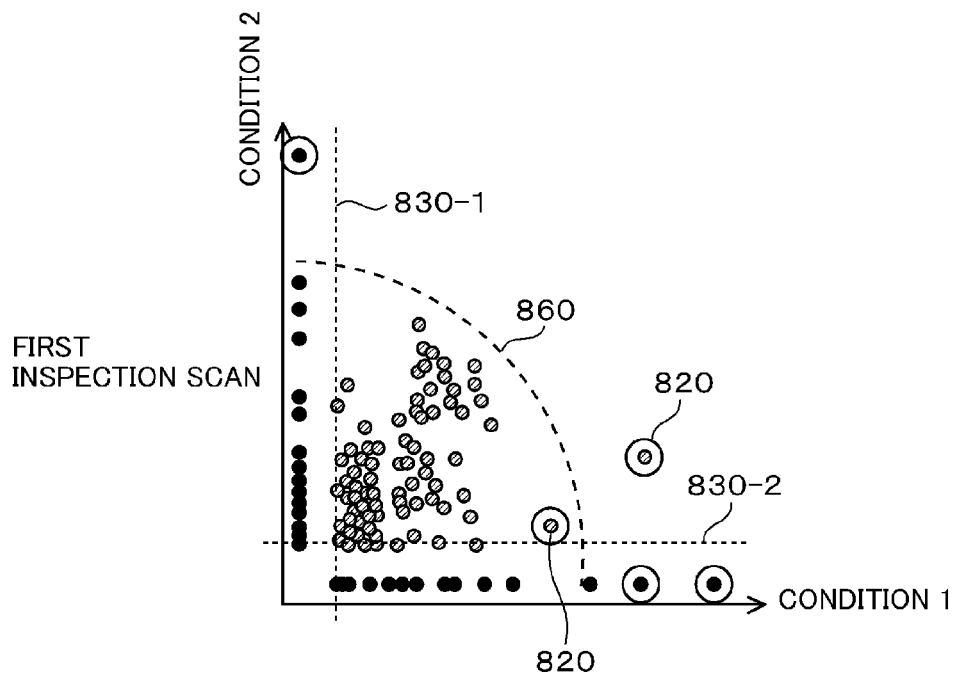
FIG. 8E is another graph illustrating a distribution in a two-dimensional space of first and second conditions of a defect detected by first inspection scanning.
Figure 8F:
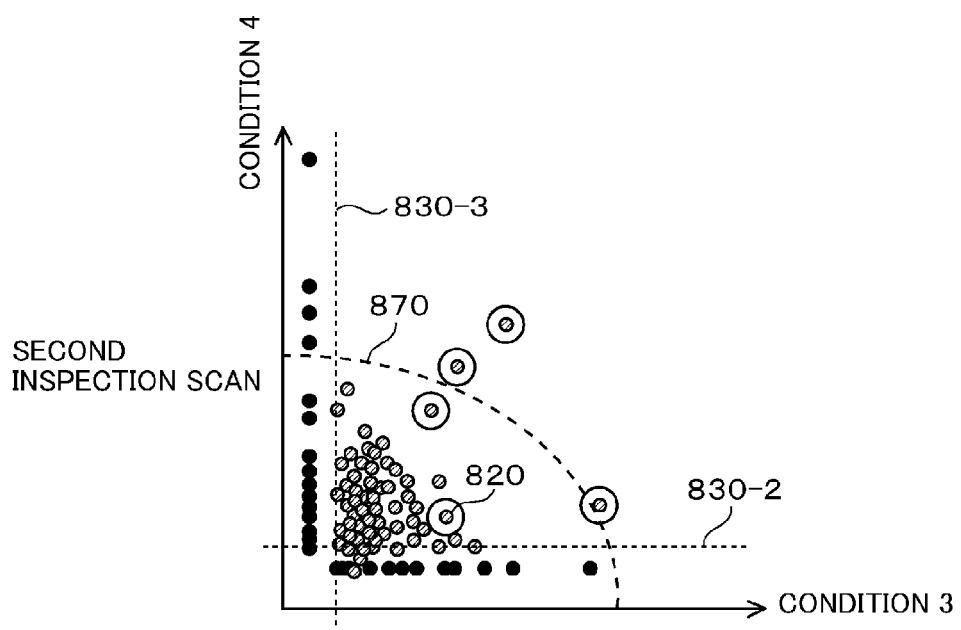
FIG. 8F is another graph illustrating a distribution in a two-dimensional space of third and fourth conditions of a defect detected by second inspection scanning.

FIG. 8A illustrates the feature space in all inspections of multiple times, but FIGS. 8E and 8F illustrate processing of the deviation amount detecting section 730 of separating the feature space of FIG. 8A into the feature spaces of the respective inspections (the first inspection and the second inspection). In the examples illustrated in FIGS. 8A, 8E, and 8F, both points at which detection is performed using a plurality of thresholds, that is, the thresholds 830-1, 830-2, 830-3, and 840-4 and a point at which detection is performed using any one threshold are illustrated. For data of a condition in which a threshold is not exceeded, coordinates in the feature space is generally ambiguous, but it is possible to obtain the coordinates through the defect candidate associating section 720 of FIG. 7A. In other words, for data in which a threshold is exceeded in any one condition, it is possible to employ a configuration of accessing data of the defect candidate extracting section 130 for data detected at the same imaging timing and outputting a corresponding position as a defect candidate even when there is no data in which a threshold is exceeded.

Through the present mechanism, it is possible to delete data detected only one condition, and it is possible to obtain an accurate position in the feature space. For example, when inspections of N times are performed through the inspection device including the three detection systems, when a defect is detected through only one of the different detection systems in an I-th inspection, it is possible to detect the defect candidate and the corresponding defect even through the two remaining detection systems. However, in a J-th inspection (J differs from I), there is a case in which there is no data corresponding to the defect candidate. In other words, in an inspection of a plurality of conditions in which inspections are not performed at the same timing, even when a defect candidate is extracted in a certain condition, there is a case in which it is difficult to detect a defect in another condition.

A plane 860 in FIG. 8E and a plane 870 in FIG. 8F serve as a defect determination plane in each inspection, that is, a determination plane used for the determination performed by the deviation amount detecting section 730. When the determination plane is exceeded, an image is clipped, or a feature quantity is output. The defect determination planes 860 and 870 are set to the feature space that is obtained by each inspection and serves as a partial space based on the identification plane 850 decided in all inspections and all inspection conditions illustrated in FIG. 8A.

In the identification plane represented by the feature space illustrated in FIG. 8A, it is difficult to uniquely represent the determination plane in a feature space having a dimension illustrated in FIG. 8E or 8F which is lower than that illustrated in FIG. 8A. As a result, there is a case in which the boundary plane of the identification plane 850 is closer to the original point side than the set defect determination planes 860 and 870 according to the position of the defect candidate in the feature space illustrated in FIG. 8A. This means that the defect determination plane set in the partial space is set at a far distance from the original point, and sensitivity is decreased. Thus, it is desirable to set the boundary plane selected as the defect candidate in the feature space of FIG. 8E or 8F to the inner side further than the boundary in which the boundary plane of the identification plane 850 intersects with the space illustrated in FIG. 8E or 8F. Here, when the boundary plane is set to the inner side too much, since the number of defect candidates is extremely increased, a restriction is applied according to the number of defect candidates or the like.

For data 820 of a second inspection illustrated in FIG. 8F, although the position of the defect determination plane (the boundary plane) 870 is shifted to the outside (the arrow side of the third and fourth conditions) so that many defects are detected, it is difficult to enable more defects to be detected unless the number of detected nuisances is significantly increased. In this regard, sample plane coordinates of the defect candidate deviated from the defect determination boundary plane such as data 820 in a first inspection illustrated in FIG. BE are stored, and data having the same coordinates is regarded as the defect candidate, and data subsequent thereto illustrated in FIG. 8F is secured.

Figure 9:
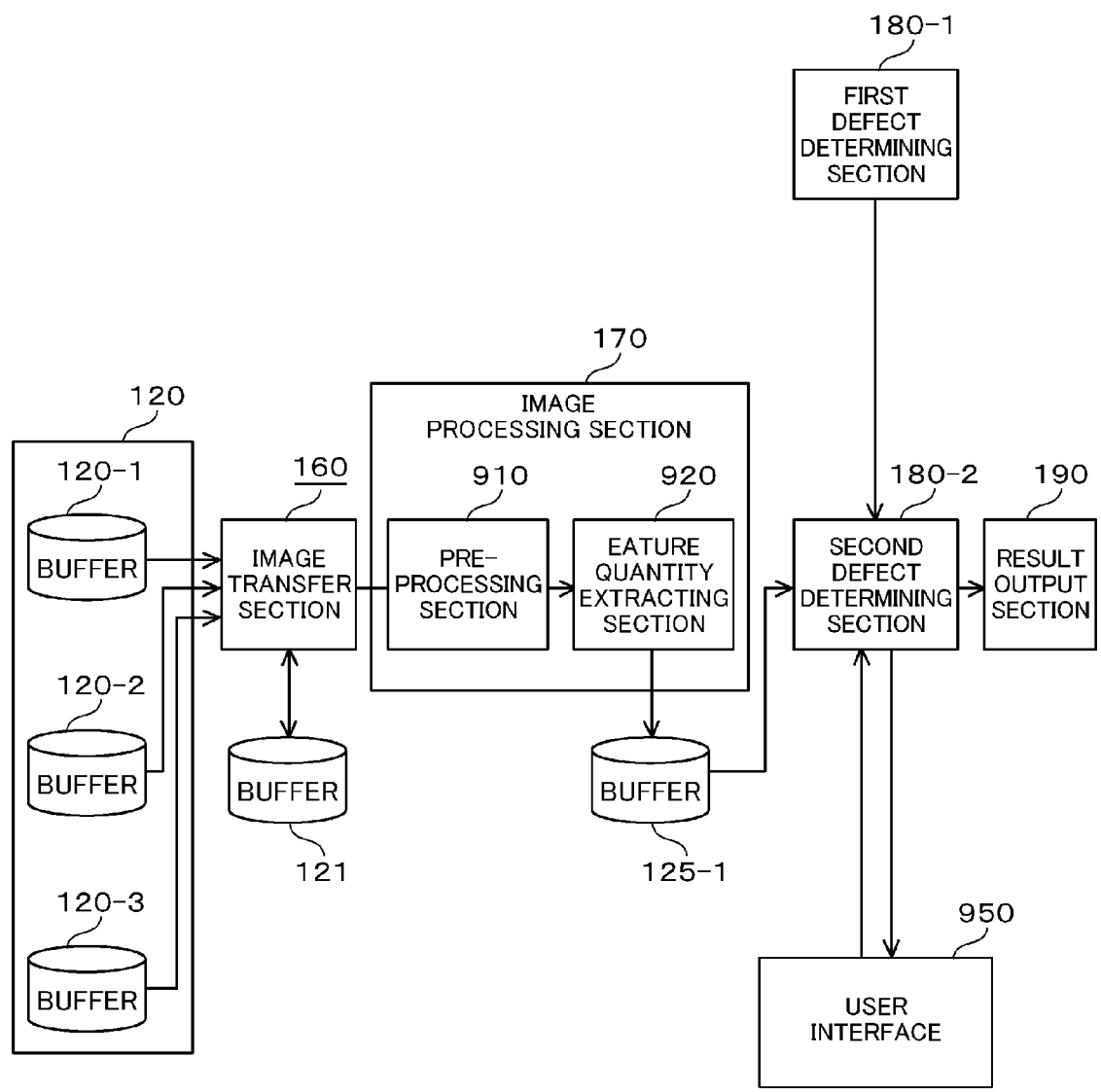
FIG. 9 is a block diagram illustrating an exemplary configuration of an image processing section in the configuration of the defect inspection device of FIG. 1B according to the first modified example of the first embodiment of the present invention.

FIG. 9 is a diagram illustrating the image storing buffer section 120 and an exemplary configuration of the image processing section 170 in the defect inspection device according to the first modified example of the first embodiment of the present invention. The control section 150 receives position information of the defect candidate determined to be the deviation amount by the defect candidate selecting section 140, and sets an image clipping position for partially clipping the inspection image that is acquired by the image acquiring section 110 and stored in the image storing buffer section 120. Defect clipping is performed in all the buffers 120-1, 120-2, and 120-3 of the image storing buffer section 120, and the detection image serving as the inspection target region including the defect candidate and the reference image serving as the comparison target are clipped for each defect candidate. At this time, the same image clipping position is set to all the buffers 120-1, 120-2, and 120-3 even for the defect candidate determined to be a single defect through the defect candidate selecting section 140.

The image transfer section 160 receives the partial image data at the image clipping position decided by the control section 150 from the buffers 120-1, 120-2, and 120-3 of the image storing buffer section 120, transfers the image to a buffer 121, and transfers the image to a pre-processing section 910 configuring the image processing section 170 according to a control signal (not illustrated) of the control section 150. The pre-processing section 910 performs an image alignment of a sub pixel unit, brightness deviation correction between respective pieces of image data, and the like on the received partial image data, that is, the partial image data of the image storing buffer 120.

The feature quantity extracting section 920 receives the partial image data of the detection image and the reference image in each image acquisition condition from the pre-processing section 910, and calculates a feature quantity of the defect candidate. Examples of the feature quantity to be calculated include (1) brightness, (2) a contrast, (3) a intensity difference, (4) a brightness dispersion value of a neighboring pixel, (5) a correlation coefficient, (6) an increase or a decrease in brightness with a neighboring pixel, and (7) a secondary differentiation value.

The feature quantity extracting section 920 stores the feature quantities in the buffer 125-1 until a certain number of defect candidates are stored or inspections of multiple times are ended in the defect candidate extracting section 130. The second defect determining section 180-2 receives the feature quantity of the defect candidate stored in the buffer 125-1, generates the feature space, and performs classification based on the defect candidate distribution in the feature space.

Here, the second defect determining section 180-2 selects a feature quantity used for the determination performed by the first defect determining section 180-1 for each defect type or for each defect region using the temporary determination result determined by the first defect determining section 180-1, and calculates the feature space. This is because since the determination by the first defect determining section 180-1 using the feature space (a) has features in which the number of defect candidates stored in the buffer 125-2 is much larger than the number of defect candidates stored in the buffer 125-1, (b) the defect determination boundary plane has already satisfied a specific relation as indicated in (Formula 3) and (Formula 4), and (c) the feature quantity to be used can be easily estimated based on a formula and a statistic other than a defect candidate position, it is easy to detect a defect in inspections of multiple times, particularly in the actual defect, as a defect candidate in a number of inspection conditions, and it is easy to estimate and determine the feature quantity in the multi-dimensional space even when it is difficult to detect a defect.

On the other hand, the feature quantity of the image data stored in the buffer 125-1 does not satisfy this. In this regard, the defect determination is performed based on the result determined by the first defect determining section 180-1 in advance after reducing the feature used in the feature space, that is, without using the feature quantity of the inspection condition that is unnecessary for the determination. As a result, in the multi-condition inspection, even when there is a defect candidate having no correspondence relation, it is possible to stably perform the defect determination. Here, the second defect determining section 180-2 is connected with a user interface 950 and thus can receive a teaching from the user. The user can teach a DOI that is desired to be detected through the user interface 950. The result output section 190 outputs a determination result obtained by the second defect determining section 180-2 or a defect classification result.

At the same time, the teaching of the first defect determining section 180-1 by the user interface 950, is performed, and thus it makes easy to set a recipe. For example, G(k) of (Formula 3) is optimized using an algorithm such as a support vector machine as a method of optimizing the boundary plane of the first defect determining section 180-1. Similarly, the boundary plane is calculated by the deviation amount detecting section 730 through optimization of G(k), and the boundary plane of the defect candidate extracting unit 130-1 is set through optimization of A(k), B(k), and C(k) of (Formula 2).

Figure 10A:
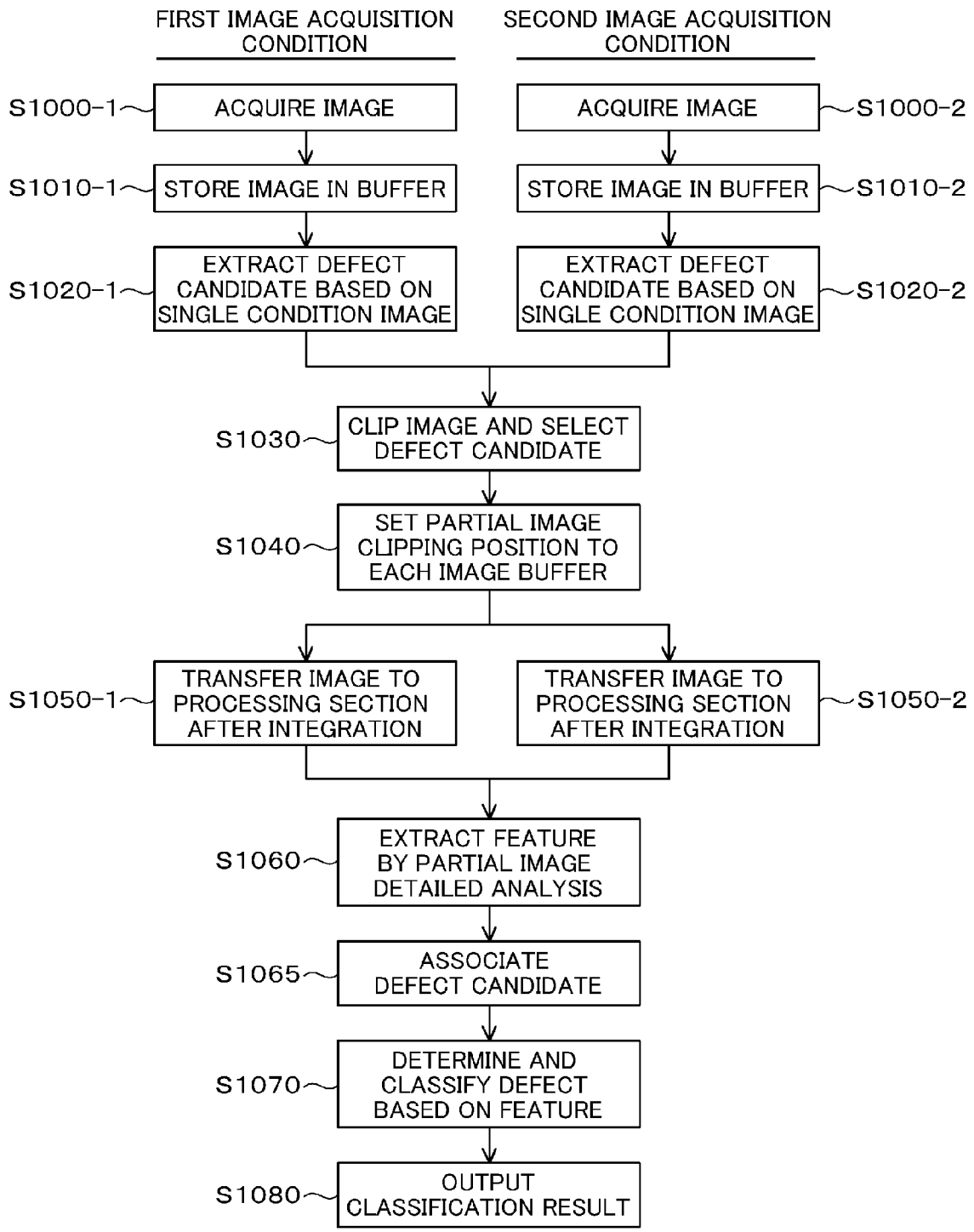
FIG. 10A is a flowchart illustrating an example of a defect determination flow in the defect inspection devices according to the first embodiment and the first and second modified examples of the present invention.

FIG. 10A is a diagram illustrating an example of a defect inspection process flow in the defect inspection devices according to the first embodiment and the first and second modified examples of the present invention, and in this process flow, two image acquisition conditions are employed. First, the image acquiring section 110 simultaneously acquires images at the same position on the sample in the respective image acquisition conditions (S1000-1 and S1000-2), and stores the acquired images in the image storing buffers 120-1 and 120-2 (S1010-1 and S1010-2). Then, the defect candidate extracting section 130 extracts defect candidates from the images acquired in the respective conditions (S1020-1 and S1020-2). Then, in the defect candidate selecting section 140, by associating the defect candidates and the respective image acquisition conditions and calculating the deviation amount, defect candidate selection is carried out (S1030). Then, the defect candidate selecting section 140 sets a partial image clipping position to the image storing buffer section 120 through the control section 150 (S1040), and transfers partial image data from the image storing buffer section 120 to the image processing section 170 through the image transfer section 160 (S1050-1 and S1050-2). The image processing section 170 integrates the images of the respective conditions, and extracts an image feature quantity of the defect candidate (S1060). Then, the defect determining section 180 associates the defect candidates detected in the different acquisition conditions based on the same defect candidate using coordinates of the defect candidates of the respective inspections (S1065). Then, the associated defect candidates are plotted in the multi-dimensional feature quantity space, and defect determination of determining a defect by comparing the defect candidates plotted in the multi-dimensional feature quantity space with a previously set threshold or classification of the defect candidate determined as a defect are performed (S1070). The result output section 190 outputs the defect detection result (S1080).

Figure 10B:
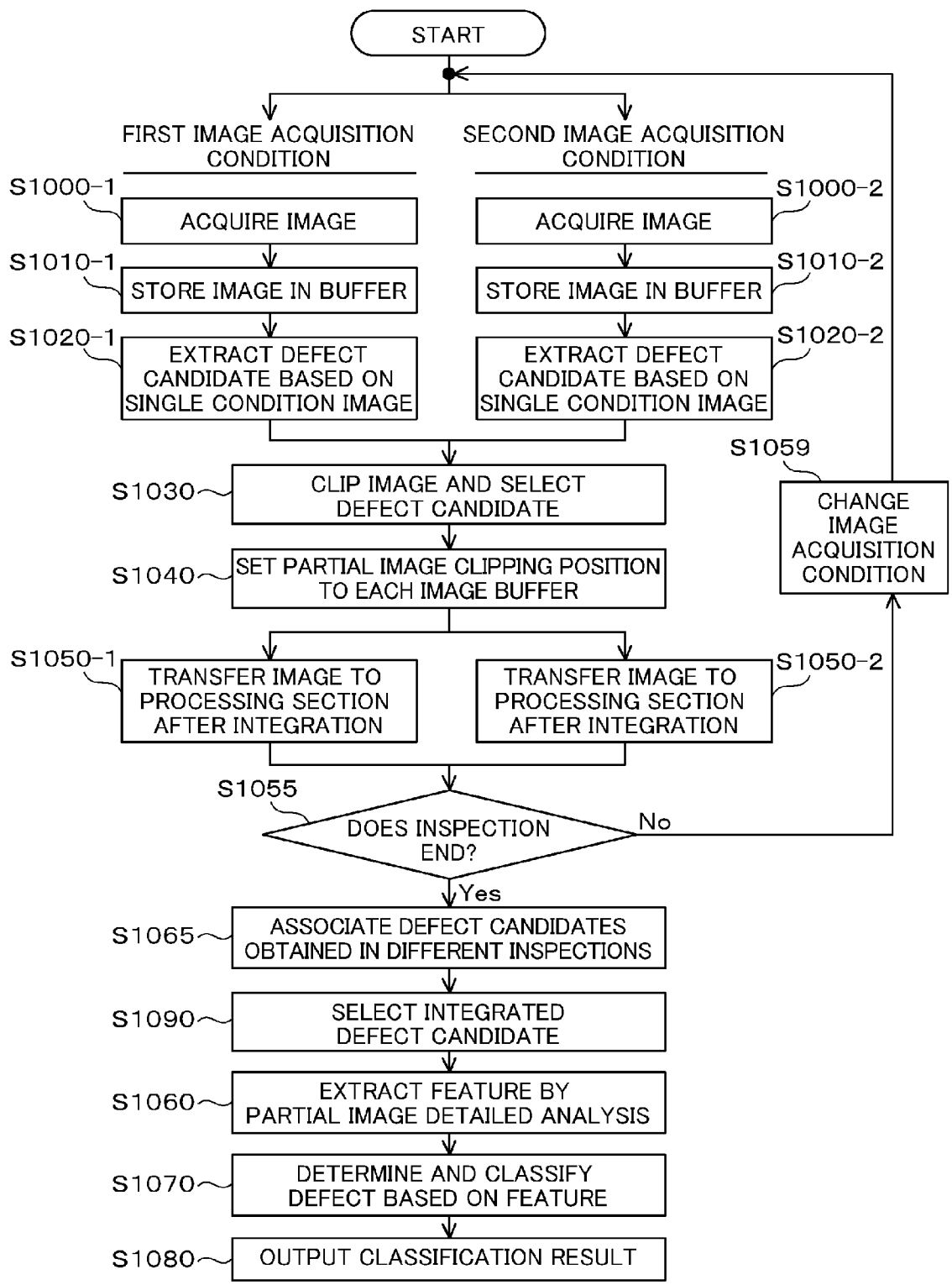
FIG. 10B is a diagram illustrating an example of a defect determination flow in the defect inspection devices according to the first embodiment and the first and second modified examples of the present invention, and illustrates a flowchart when a plurality of images are acquired while changing an image acquisition condition.

FIG. 10B illustrates an example of the flow in which inspections of multiple times are performed while the inspection result of FIG. 10A is a single inspection result, and an inspection result in which the inspection results are integrated is output. A description will proceed focusing on only a difference with that of FIG. 10A. After the image transfer to the image processing section 170 in S1050-1 and S1050-2 ends, an end determination is performed in 51055, and when the inspection does not end yet, in S1059, the image acquisition condition is changed, and the image acquisition of S1000-1 and S1000-2 is performed again. When the inspection is determined to end in 51055, the defect candidates obtained in the different inspections are associated (S1065). In S1090, the first defect determining section 180-1 performs an integrated defect candidate selection based on the feature quantity, and in S1060, the feature extraction is performed by partial image detailed analysis, and a defect candidate that performs the defect determination, a feature quantity used for the determination, and a conditional image used for a calculation of a feature quantity are selected. Then, similar to the flow shown in FIG. 10A, the defect determination and classification process is performed based on the feature (S1070), and a classification result output process is performed (S1080).

FIG. 10C illustrates an example in which the defect candidate extraction processes of S1020-1 and S1020-2 of FIG. 10B are performed by a single processing unit in a hardware manner (S1020). As a result, the deviation amount detecting section of FIG. 7A can perform the deviation amount detection without lack of the feature quantity using the defect candidate obtained from the image detected in a plurality of conditions, and thus it is possible to improve the sensitivity. The remaining process is similar to the flow shown in FIG. 10B.

FIG. 10D illustrates the flow in which the process from the image clipping and the defect candidate selection (S1030) to the image transfer to the processing section after the detailed analysis (S1050) in the flow of FIG. 10C is not performed. In the process flow described above with reference to FIG. 10C, the integrated defect candidate selection (S1090) is the pre-processing of clipped image detailed analysis, but in the process flow illustrated in FIG. 10D, final defect determination is performed in the integrated defect candidate selection (S1090). Even in the process flows described above with reference to FIGS. 10A and 10B, similarly, a mode in which the determination (from S1030 to S1050-1 and S1050-2) based on the clipped image is omitted, and the determination of S1090 is used as the final determination is provided.

A process flow illustrated in FIG. 10E is a process flowchart based on the configuration of FIG. 1C described in the second modified example of the first embodiment. The sequence in which the image is clipped, the detailed analysis is performed, and the transfer to the image processing section 170 is performed (S1000-1 and S1000-2 to S1050-1 and S1050-2) are the same as the process described above with reference to FIG. 10B. But the feature extraction process based on the partial image detailed analysis in S1060 is performed in each inspection (for each image acquisition condition) after the process of S1050-1 and S1050-2, and in FIG. 10E, temporary defect determination and classification based on a partial image feature in S1075 is performed in each inspection (for each image acquisition condition), instead of the final defect determination of S1070 in the process flow of FIG. 10B. In S1075, a defect likelihood is calculated together with the temporary defect determination. The inspection is performed multiple times while changing an imaging condition in S1059, and the defect candidates obtained in the respective inspections are associated in S1065. Thereafter, the feature quantity change performed by the feature quantity changing section 185 of FIG. 1C is performed in 51094, integrated defect determination is performed based on the feature quantities obtained in a plurality of inspections in S1090, and a classification result is output in S1080.

Figure 11:
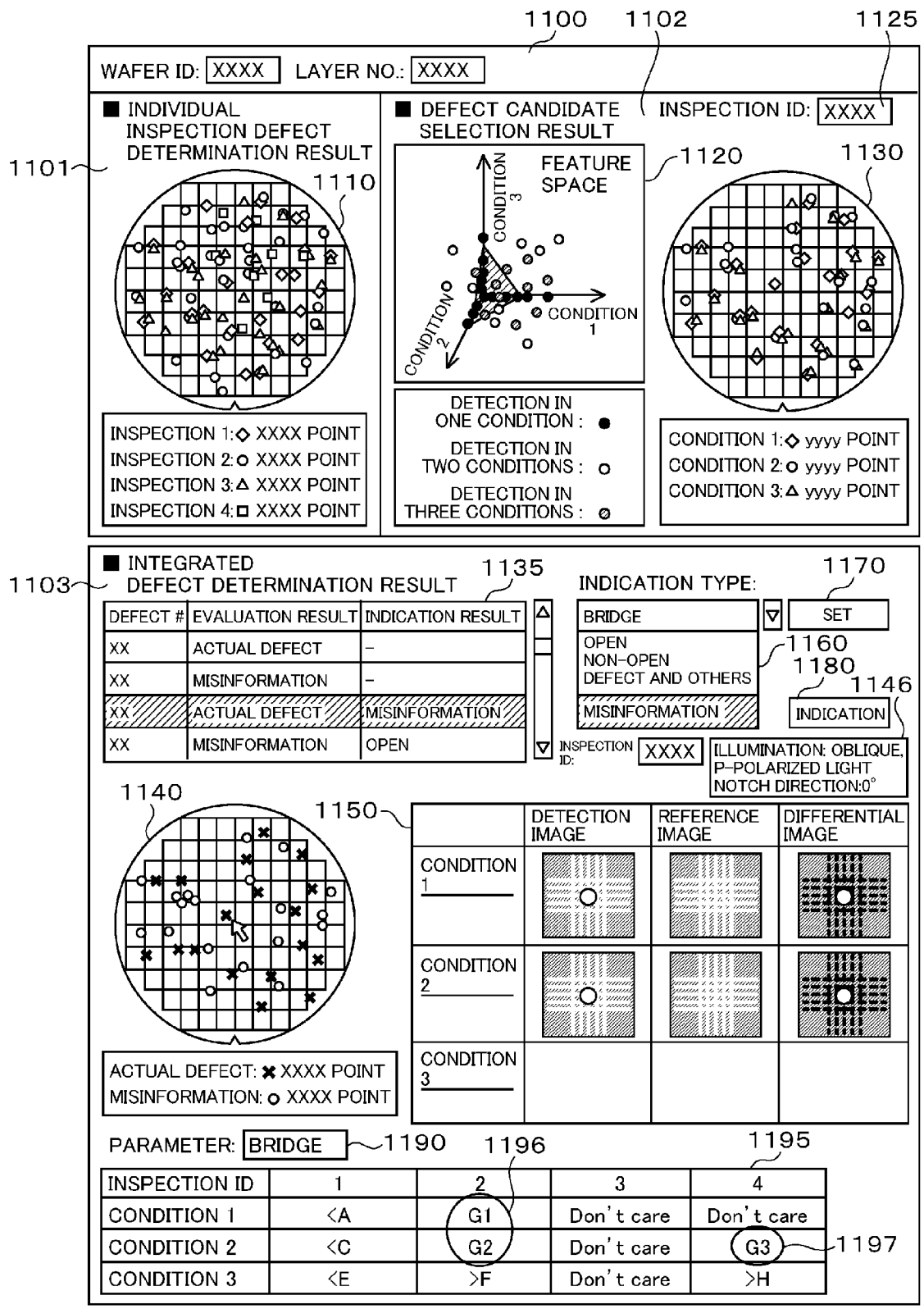
FIG. 11 is a front view of a screen illustrating an extension display example of a GUI for teaching defect candidate in the defect inspection devices according to the first embodiment and the first and second modified examples of the present invention.

FIG. 11 is a diagram illustrating an example of a graphic user interface (GUI) 1100 displayed on the user interface 950 in the defect inspection devices according to the first embodiment and the first and second modified examples of the present invention. The GUI 1100 is configured to include an individual inspection defect determination result display region 1101, a defect candidate selection result display region 1102, and an integrated defect determination result display region 1103.

The user causes a wafer map 1110 indicating a result obtained by the defect determination in the second defect determining section 180-2 to be displayed on the individual inspection defect determination result display region 1101 of the GUI 1100, and causes a feature space 1120 in which the deviation amount of the defect candidate is determined through the first defect determining section 180-1 for each inspection ID input to an inspection ID input region 1125 by the user and for each inspection condition and a wafer map 1130 indicating defect candidates to be output to the image processing section 170 after the defect candidate selection results are integrated to be displayed on the defect candidate selection result display region 1102. Further, a wafer map 1140 indicating a result of performing classification of actual defects and false information through the first defect determining section 180-1 after integrating the inspection results obtained in the respective inspections is displayed on the integrated defect determination result display region 1103.

An evaluation/teaching result display region 1135 is a region on which each defect candidate ID, an evaluation result, and a taught defect attribute are displayed, and when a screen is designated by a pointer of the GUI, an image of a defect candidate corresponding to an inspection ID input and designated from an inspection ID input portion 1145 is displayed on an image display region 1150 for each detection condition. In FIG. 11, an image is not displayed for a third condition in which no defect candidate was detected. An illumination condition used in the inspection ID and an imaging condition such as a wafer rotation direction are displayed on an illumination/imaging condition display region 1146.

A teaching type selection region 1160 is a region in which a defect attribute for teaching is selected, and any one of defect attributes displayed on the designation type selection region 1160 is designated by a pointer, the set button 1170 is clicked through the pointer, and thus a defect attribute is taught for a designated defect ID. 1180 is a teaching button, and the determination boundary used to determine a defect and false information for each defect attribute in the defect candidate detecting section 330 through the parameter setting section 340 is set based on the result of teaching by clicking the designation button 1180 through the pointer of the GUI. A support vector machine or linear determination is used as the determination boundary setting method. An indication result can be checked through display content of an inspection condition display region 1195.

Information displayed on the inspection condition display region 1195 indicates a degree of contribution to an inspection of each inspection condition of each inspection ID. Data 1196 and 1197 displayed on the inspection condition display region 1195 are typically values of G(k) of Formula 4 obtained by the teaching. The user can manually input a parameter to the parameter input region 1190 as well, and a degree of deviation on a reference variation of a detection condition of each inspection that is known in advance or information indicating that a specific detection condition does not contribute to determination of a specific defect attribute may be input to the parameter input region 1190.

According to the present embodiment, local image data including a defect candidate among a large amount of image data detected by a plurality of detection systems is extracted, integrated, and processed. Thus, it is possible to increase the defect detection sensitivity without extremely increasing an amount of data, and it is possible to perform sample imaging and image processing in parallel. Accordingly, it is possible to inspect a minute defect at a high speed with a high degree of sensitivity.

Second Embodiment

Figure 12:
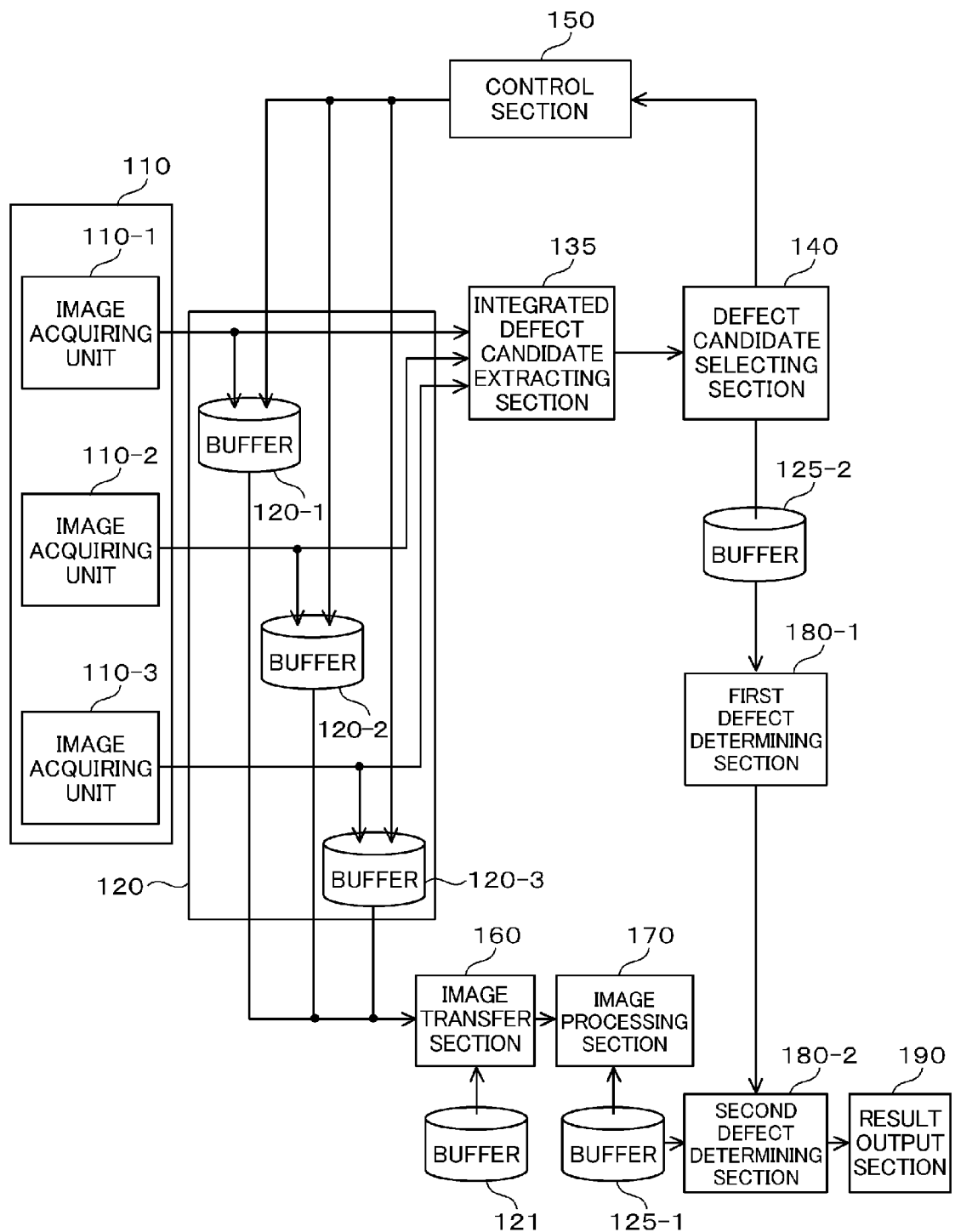
FIG. 12 is a block diagram illustrating an exemplary overall schematic configuration according to a defect inspection device according to a second embodiment of the present invention.

FIG. 12 is a block diagram illustrating a schematic configuration of a defect inspection device according to a second embodiment, and illustrates a configuration obtained by partially changing the configuration of the first embodiment described above with reference to FIG. 1B. Components having the same reference numerals as in the first embodiment have the same functions as those described in the first embodiment. In the configuration of the first embodiment illustrated in FIG. 1B, the respective defect candidate extracting units 130-1, 130-2, and 130-3 of the defect candidate extracting section 130 extract the defect candidates from the image data acquired by the image acquiring units 110-1, 110-2, and 110-3 of the image acquiring section 110, but in the configuration of the second embodiment illustrated in FIG. 12, an integrated defect candidate extracting section 135 performs an integrated extraction.

The integrated defect candidate extracting section 135 includes a configuration of processing each image data which corresponds to the defect extracting units 130-1, 130-2, and 130-3 of the first embodiment therein, but when a defect candidate detected in an image from any one of the image acquiring units 110-1, 110-2, and 110-3 of the image acquiring section 110 is output at the time of outputting defect candidate, although a defect candidate is not selected from an image acquired by another image acquiring unit, a feature quantity of the defect candidate is output. Further, FIG. 10C or FIG. 10D is typically applied as the flow.

Even in the present embodiment, the same effects as in the first embodiment can be obtained.

Third Embodiment

A configuration illustrated in FIG. 13A according to a third embodiment is an example in which the configuration described with reference to FIG. 12 in the second embodiment is modified. In the configuration illustrated in FIG. 12, the inputs from the image acquiring units 110-1, 110-2, and 110-3 of the image acquiring section 110 are stored in the buffers 120-1, 120-2, and 120-3 of the buffer section 120, and the clipped images from the buffers 120-1, 120-2, and 120-3 are transferred to the image transfer section 160. In the first embodiment, in the configuration illustrated in FIG. 1B, the defect candidate extracting units 130-1, 130-2, and 130-3 of the defect candidate extracting section 130 extract the defect candidates independently, and thus when a defect candidate is determined by any one of the defect candidate extracting units 130-1, 130-2, and 130-3, the images clipped from the images stored in the buffers 120-1, 120-2, and 120-3 of the buffer section 120 can be transferred to the image transfer section 160.

Figure 13A:
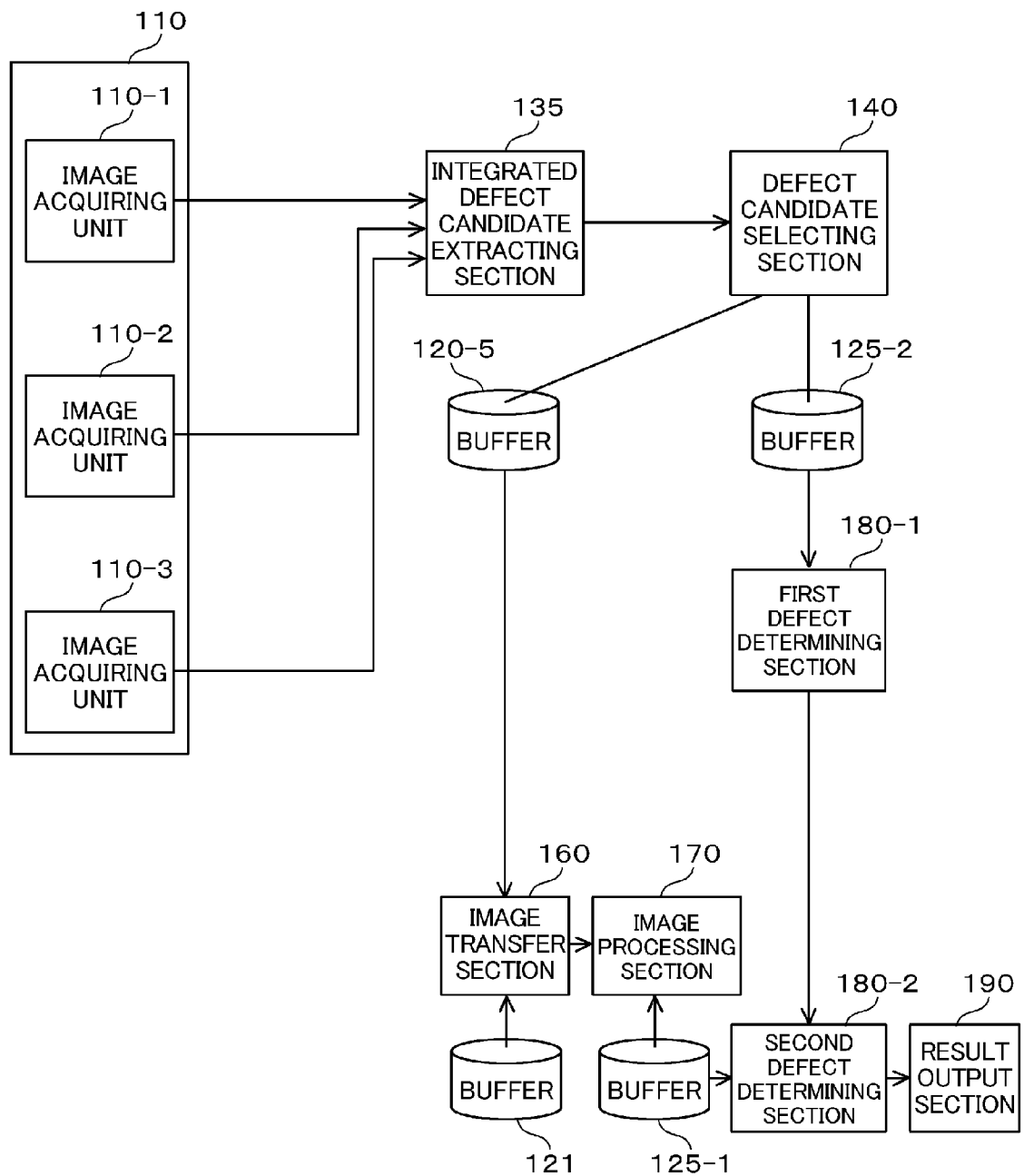
FIG. 13A is a block diagram illustrating an exemplary configuration of a defect inspection device according to a third embodiment of the present invention.

On the other hand, in the configuration illustrated in FIG. 13A in which the defect candidate extracting units 130-1, 130-2, and 130-3 of the defect candidate extracting section 130 described in the first embodiment are replaced with the integrated defect candidate extracting section 135, the integrated defect candidate extracting section 135 extracts defect candidates from the images transferred from the image acquiring units 110-1, 110-2, and 110-3, and clips a neighboring image including the extracted defect candidate. Then, the clipped defect candidate and the neighboring image are transferred from the integrated defect candidate extracting section 135 to the defect candidate selecting section 140, and the clipped image is stored in a buffer 120-5.

A configuration illustrated in FIG. 13B is a modified example of FIG. 13A. The configuration illustrated in FIG. 13A is an embodiment having a configuration different from the configuration of the first embodiment described with reference to FIG. 1B. However, the configuration illustrated in FIG. 13B is an embodiment having a configuration different from the configuration of the first embodiment described with reference to FIG. 10, and similarly to the configuration described with reference to FIG. 10, the second defect determining section 180-2 is executed as the pre-processing of the first defect determining section 180-1, and the second defect determining section 180-2 performs final defect determination. A buffer 125-3 and a feature quantity changing section 185 that are newly added perform the same operations as those described with reference to FIG. 10 in the first embodiment.

FIG. 16 illustrates an example of misalignment correction of a defect candidate by the first defect determining section 180-1. Defect candidates 1630 and 1640 used for misalignment detection are selected from a map 1610 of defect candidates detected from an image acquired in a first image acquisition condition and a map defect candidate 1620 of defect candidates detected from an image acquired in a second image acquisition condition, and a deviation amount is calculated from the selected defect candidate. Based on the obtained deviation amount, a map 1650 in which the misalignment of the defect candidates in the maps 1610 and 1620 of the first and second image acquisition conditions is corrected is generated (1650). Here, the map 1650 need not be necessarily generated, and it is desirable to store data in which misalignment on each defect candidate is corrected.

In the first to third embodiments, the example in which the dark-field inspection device is employed as the inspection device has been described. However, the first to third embodiments can be applied to all types of inspection devices such as a bright-field inspection device or an SEM type inspection device, and it is possible to perform image acquisition and defect determination through the plurality of types of inspection devices as a plurality of image acquisition conditions.

Fourth Embodiment

FIG. 14 is a diagram illustrating an exemplary configuration of an SEM type inspection device 110" as another example of the configuration of the image acquiring section 110. Components performing the same operation or operation equivalent to the dark-field type inspection device described with reference to FIG. 2 in the first embodiment and the first and second modified examples are denoted by the same reference numerals.

In a configuration of the SEM type inspection device 110" illustrated in FIG. 14, 1410 indicates an electron beam source that emits electron beams, 1420 and 1430 indicate condenser lenses that focus the electron beams emitted from the electron beam source 1410, 1440 indicates an electron beam axis adjuster that adjusts astigmatism or misalignment of the focused electron beams, 1480 indicates a reflecting plate having a primary electron beam passage hole for passing the electron beams whose astigmatism or misalignment has been adjusted, 1450 and 1460 indicate scanning units that scan the electron beams, 1470 indicates an object lens, and 1490 indicates a reflected electron detector that detects reflected electrons reflected by the reflecting plate 1480 having the primary electron beam passage hole among reflected electrons generated in a wafer 210 irradiated with the electron beams. 1491 and 1492 indicate secondary electron detectors that detect secondary electrons generated in the wafer 210 irradiated with the electron beams, and 1500, 1501, and 1502 indicate A/D converters that converts a detection signal obtained by detecting the reflected electrons or the secondary electrons through the reflected electron detector 1490 or the secondary electron detectors 1491 and 1492 into a digital signal, and 270 indicates a control section that receives signals output from the A/D converters 1500, 1501, and 1502, transmits the detection signal to the defect candidate extracting section 130, and controls the SEM type inspection device 110" in general.

In the SEM type inspection device 110" of this configuration, the electron beams that are emitted from the electron beam source 1410 pass through the condenser lens 1420 and 1430 and then undergo astigmatism or misalignment correction performed by the electron beam axis adjuster 1440. The scanning units 1450 and 1460 deflect the electron beams and control the position at which the electron beams are irradiated, and thereafter the electron beams are focused by the object lens 1470 and irradiated on an imaging target region 1400 of the wafer 210. As a result, the secondary electrons and the reflected electrons are emitted from the imaging target region 1400, and the secondary electrons and the reflected electrons collide with the reflecting plate 1480 having the primary electron beam passage hole, and thus the secondary electrons are detected by the reflected electron detector 1490. Further, the secondary electrons generated from the imaging target region are detected by the secondary electron detectors 1491 and 1492. As a result, the electrons are detected by the electron detectors arranged at different positions in three directions including the imaging target region 1400.

The secondary electrons and reflected electrons detected by the reflected electron detector 1490 and the secondary electron detectors 1491 and 1492 are converted into a digital signal through the A/D converters 1500, 1501, and 1502, and the digital signal is transferred to the control section 270 and the defect candidate extracting section 130. A combination of the electron detectors 1490, 1491, and 1492 and the A/D converters 1500, 1501, and 1502 can be regarded to be the same as the image acquiring units 110-1, 110-2, and 110-3 of the image acquiring section 110 illustrated in FIGS. 1A to 10, FIG. 12, FIG. 13A, and FIG. 13B. Further, in the case of an SEM, by inspecting the same inspection target multiple times while changing a condition including an acceleration voltage of the electron beams or a potential difference between the wafer 210 and the object lens 1470 as the detection condition, the inspection sensitivity can be improved through the same method as before.

The invention of the present inventor has been specifically described above based on the embodiments, but the present invention is not limited to the above embodiments, and various changes can be made within the scope not departing from the gist.

REFERENCE SIGNS LIST

110 Image acquiring section
120 Image storing buffer
125 Feature quantity storing buffer
130 Defect candidate extracting section
140 Defect candidate selecting section
150 Control section
160 Image transfer section
170 Image processing section
180 Defect determining section
190 Result output section
210 Wafer
220 Stage
230 Controller
240 Illumination system
250 Detection system
310 Pre-processing section
320 Image memory section
330 Defect candidate detecting section
340 Parameter setting section
350 Control section
410 Detection image
420 Reference image
430 Aligning section
440 Feature quantity calculating section
450 Feature space forming section
460 Deviation pixel detecting section
710 Misalignment detecting/correcting section
720 Defect candidate associating section
730 Deviation value detecting section
910 Pre-processing section
920 Feature quantity extracting section
930 Feature quantity storage section
940 Defect classifying section
950 User interface

The invention claimed is:

1. A defect inspection method, comprising:
    imaging a same region of a sample in a plurality of image acquisition conditions using an image acquiring section comprising a plurality of image acquiring portions each of which is configured for a different image acquisition condition with respect to each other to acquire a plurality of images for said same region of the sample;
    storing said plurality of images in a plurality of image storing buffers corresponding to said plurality of image acquiring portions;
    extracting a defect candidate from each of the plurality of images using a defect candidate extracting section comprising a plurality of defect extracting portions each coupled to a corresponding one of the plurality of image storing buffers;
    clipping a partial image including the extracted defect candidate and a neighboring image of the defect candidate from the plurality of acquired images stored in a corresponding plurality of said image storing buffers using a controller configured to clip said partial image based on coordinate position information of the extracted defect candidate;

obtaining feature quantities of the defect candidates in the plurality of clipped partial images using at least one defect determining section, said feature quantities comprising one or more of a difference between an inspection image and a reference image, a brightness variation between dies having same coordinates, a differential image variation in a pattern similar to a defect candidate of the reference image, and an edge strength of the reference image;

associating, using said at least one defect determining section, the defect candidates that have the same coordinates and are detected in conditions in which the image acquisition condition is different among the extracted defect candidate;

extracting, using a defect extracting section, a defect from among the associated defect candidates based on multi-dimensional feature quantity space data of feature quantities of the associated defect candidates; and outputting using a display information of the extracted defect.

2. The defect inspection method according to claim 1, wherein the acquiring of the plurality of images for the same region of the sample is performed multiple times while changing the image acquisition condition of the image acquiring section, and in the outputting of the information of the defect, the defect candidates extracted from the images acquired multiple times while changing the image acquisition condition are associated and integrated by the defect extracting section, and information of an integrated defect is output using the display.

3. The defect inspection method according to claim 1, wherein false information is removed by the defect determining section based on coordinate information of the defect candidate from among the associated defect candidates, and multi-dimensional feature quantity space information is allocated to the defect candidate from which the false information has been removed.

4. The defect inspection method according to claim 1, wherein the extracted defect is classified by the defect extracting section, and information of the classified defect is output using the display.

5. A defect inspection device, comprising:

an image acquiring section configured to image a same region of a sample in a plurality of image acquisition conditions and to acquire a plurality of images for the same region of the sample, the image acquiring section comprising a plurality of image acquiring portions each of which is configured to have a different image acquisition condition with respect to each other;

a plurality of image storing buffers corresponding to said plurality of image acquiring portions which store said plurality of images;

a defect candidate extracting section configured to extract a defect candidate in each of the plurality of images;

a controller configured to clip a partial image including the extracted defect candidate and a neighboring image of the defect candidate from the plurality of images acquired by the image acquiring section based on position information of the defect candidate extracted by the defect candidate extracting section, at least one defect determining section configured to obtain feature quantities of the defect candidates in the plurality of clipped partial images, said feature quantities comprising one or more of a difference between an inspection image and a reference image, a brightness variation between dies having same coordinates, a differential image variation in a pattern similar to a defect candidate of the reference image, and an edge strength of the reference image, wherein the at least one defect determining section is further configured to associate defect candidates that have the same coordinates and are detected in conditions in which the image acquisition condition is different among the defect candidate extracted by the defect candidate extracting section;

a defect extracting section configured to extract a defect from among the defect candidates associated using the defect candidate associating section based on multi-dimensional feature quantity space data of feature quantities of the associated defect candidates; and a display that outputs information of the defect extracted by the defect extracting section.

6. The defect inspection device according to claim 5, wherein the image acquiring section performs the acquiring of the plurality of images for the same region of the sample multiple times while changing the image acquisition condition, the defect extracting section associates and integrates the defect candidates extracted from the images acquired multiple times while changing the image acquisition condition through the image acquiring section, and the display outputs information of a defect integrated by the defect extracting section.

7. The defect inspection device according to claim 6, wherein the at least one defect determining section removes false information based on coordinate information of the defect candidate from among the defect candidates associated by the defect candidate associating section, and allocates multi-dimensional feature quantity space information to the defect candidate from which the false information has been removed.

8. The defect inspection device according to claim 6, wherein the defect extracting section further classifies the extracted defect, and the display outputs information of the classified defect.

* * * * *